(12) United States Patent
Niesslein et al.

(10) Patent No.: US 8,856,668 B2
(45) Date of Patent: Oct. 7, 2014

(54) DRUG DELIVERY DEVICES AND RELATED SYSTEMS AND METHODS

(75) Inventors: Michael Niesslein, Gibsonia, PA (US); Marisette Edwards, Verona, PA (US); Tom Monahan, Cranberry Township, PA (US); Douglas Mark Zatezalo, Allison Park, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 203 days.

(21) Appl. No.: 13/335,280

(22) Filed: Dec. 22, 2011

(65) Prior Publication Data
US 2013/0167052 A1 Jun. 27, 2013

(51) Int. Cl.
*G06F 3/048* (2013.01)
(52) U.S. Cl.
USPC .......................................................... 715/764
(58) Field of Classification Search
USPC .......................................................... 715/764
See application file for complete search history.

(56) References Cited

U.S. PATENT DOCUMENTS

| | | | |
|---|---|---|---|
| 5,309,172 | A | 5/1994 | Fox |
| 5,956,023 | A | 9/1999 | Lyle et al. |
| 7,410,475 | B2 | 8/2008 | Krensky et al. |
| 2002/0045851 | A1 | 4/2002 | Suzuki et al. |
| 2008/0034323 | A1* | 2/2008 | Blomquist .................... 715/810 |
| 2010/0280486 | A1* | 11/2010 | Khair et al. .................... 604/506 |
| 2011/0004143 | A1 | 1/2011 | Beiriger et al. |
| 2011/0144569 | A1 | 6/2011 | Britton et al. |
| 2011/0193715 | A1* | 8/2011 | Bibelhausen et al. ........ 340/683 |
| 2012/0035533 | A1 | 2/2012 | Britton et al. |

FOREIGN PATENT DOCUMENTS

| | | |
|---|---|---|
| WO | WO9625963 A1 | 8/1996 |
| WO | WO03038566 A3 | 10/2003 |
| WO | WO2011002853 A2 | 1/2011 |

OTHER PUBLICATIONS

WO 2011/002853 A2 ([US] Beiriger Michael James; Kaintz) Jan. 6, 2011.*
WO 2011/002853 A2 ([US] Beirigner Michael James; Kaintz) Jan. 6, 2011.*
WO 03/038566 A2 (Scott Lab Inc [US]; Hickle Randall, Endsley Mica [US]) May 8, 2003.*
Notification of Transmittal of the International Search Report and the Written Opinion of the International Search Authority for corresponding PCT Application No. PCT/US2012/067694, mailed Mar. 13, 2013, 15 pages.
2008K Hemodialysis Machine Operator's Manual, Fresenuis Medical Care, 2009, Fresenius USA, Inc., 184 pages.
2008T Hemodialysis Machine Operator's Manual, Fresenuis Medical Care, 2008-2010, Fresenius USA, Inc., 222 pages.
Liberty Cycler User's Guide, Fresenius Medical Care, 2008, 174 pages.

(Continued)

*Primary Examiner* — Amy Ng
*Assistant Examiner* — Andres E Gutierrez
(74) *Attorney, Agent, or Firm* — Fish & Richardson P.C.

(57) ABSTRACT

In some aspects, a method includes displaying multiple different screens on a user interface during a treatment, administering a first drug during the treatment; and while administering the first drug, displaying an identifier of the first drug in a drug identification region of the user interface. The drug identification region is present on the user interface with each of the different screens, and the identifier of the first drug is displayed in the drug identification region of the user interface regardless of which of the different screens is displayed.

19 Claims, 17 Drawing Sheets

(56) References Cited

OTHER PUBLICATIONS

Serena Operator's Manual, Program version 3.xx, English, HCEN9807, Revised Apr. 2002, 162 pages.

Sleep Safe Operating Instructions, Software Version 0.9, Part 677 805 1, Fresenius Medical Care, Aug. 2000, 133 pages.

Operator's Instructions, Fresenius 90/2 Peritoneal Therapy Cycler, P/N 470016, Rev. B, Fresenius USA, Concord, CA, 1991, 64 pages.

* cited by examiner

DRUG DELIVERY DEVICES AND RELATED SYSTEMS AND METHODS

TECHNICAL FIELD

This invention relates to drug delivery devices and related systems and methods.

BACKGROUND

When kidney failure is diagnosed, patients are typically given medication to help control the symptoms and slow the progress of the damage to the kidneys. Patients with chronic kidney failure generally take drugs to control the balance of minerals in the body and prevent a reduction of red blood cells (anemia).

Healthy kidneys produce the hormone erythropoietin (often shortened to "EPO"), which stimulates the production of red blood cells in the bone marrow. Red blood cells play a key role in the delivery of oxygen to tissues in the body. If the body does not have enough EPO, it can lead to anemia. This often causes a drop in physical and mental performance and an increased risk for cardio-vascular diseases. To prevent anemia, chronic renal patients normally receive a synthetic version of erythropoietin (also referred to as "EPO") that, like the natural erythropoietin, stimulates the production of red blood cells.

Anemia can be managed using a variety of different drugs. For example, since iron is also needed to produce red blood cells, many dialysis patients also take iron preparations. Venofer® (iron sucrose injection, USP) is indicated in the treatment of iron deficiency anemia in patients undergoing chronic hemodialysis who are receiving supplemental EPO therapy. Blood anticoagulants (e.g., heparin) can also be administered to patients during dialysis treatments to prevent blood that is circulated within dialysis machines from clotting.

Various dialysis systems and associated machines can be used to selectively administer these different drugs to reduce medical and safety complications during dialysis treatments.

SUMMARY

In one aspect of the invention, a method includes displaying multiple different screens on a user interface during a treatment, administering a first drug during the treatment, and while administering the first drug, displaying an identifier of the first drug in a drug identification region of the user interface, the drug identification region being present on the user interface with each of the different screens, and the identifier of the first drug being displayed in the drug identification region of the user interface regardless of which of the different screens is being displayed.

Implementations can include one or more of the following features.

The drug identification region can have a first appearance when the first drug is being administered such that a user can identify the first drug based on the first appearance of the drug identification region. The drug identification region can display a first color when the first drug is being administered such that a user can identify the first drug based on the first color of the drug identification region. The drug identification region can further display text when the first drug is being administered such that a user can identify the first drug based on the text in the drug identification region.

The method can further include administering a second drug during the treatment, where the drug identification region has a second appearance that is different than the first appearance when the second drug is being administered such that a user can identify the second drug based on the second appearance of the drug identification region. The drug identification region can display a second color when the second drug is being administered such that a user can identify the second drug based on the second color of the drug identification region. The drug identification region can further display first text when the first drug is being administered and second text when the second drug is being administered such that a user can identify the first and second drugs based on the first and second text, respectively, in the drug identification region.

In some implementations, the first and second drugs are administered simultaneously. A first portion of the drug identification region can have the first appearance and a second portion of the drug identification region can have the second appearance. While the first and second drugs are being administered, the first portion of the drug identification region can display a first color and a second portion of the drug identification region can display a second color.

In some implementations, the administration of the first drug is completed prior to completion of the administration of the second drug, and upon completion of the administration of the first drug, the drug identification region displays the second color and not the first color. The first portion of the drug identification region can further include first text and the second portion of the drug identification region can further include second text such that a user can identify the first and second drugs based on the first and second text, respectively.

In some implementations, the administration of the first drug is completed prior to completion of the administration of the second drug, and upon completion of the administration of the first drug, the drug identification region displays the second text and not the first text.

The method can further include administering a third drug during the treatment, where the drug identification region has a third appearance that is different than the first and second appearances when the third drug is being administered such that a user can identify the third drug based on the third appearance of the drug identification region.

In some implementations, prior to beginning administration of the first drug, the drug identification region indicates multiple different drugs to be delivered, and the appearance of the identification region indicates to the user that administration of the multiple different drugs has not yet begun.

In some implementations, each of the different screens is associated with one of multiple different tabs displayed on the user interface, and each tab is displayed on the user interface regardless of which of the different screens is being displayed. The method can further include selecting a first one of the tabs to display a first one of the screens and selecting a second one of the tabs to display a second one of the screens. The tabs are located along an edge region of the user interface.

In some implementations, one of the different tabs is the drug identification region. The different screens can include set up screens and treatment screens. The treatment can include a blood processing treatment (e.g., a hemodialysis treatment).

In some implementations, administering the first drug includes delivering the first drug from a container to a drip chamber of a blood line set.

In another aspect of the invention, a method includes delivering a drug, displaying a first screen on a user interface, while delivering the drug and displaying the first screen, identifying the drug in a drug identification region of the user interface, and while continuing to deliver the drug, displaying a second screen on the user interface and identifying the drug in the drug identification region of the user interface, where the drug identification region is at the same location on the user interface when the first screen is being displayed as when the second screen is being displayed.

Implementations can include one or more of the following features. The drug being delivered can be continuously identified in the drug identification region of the user interface while the drug is being delivered. Identifying the drug being delivered in the drug identification region of the user interface can include displaying a color associated with the drug in the drug identification region.

In a further aspect of the invention, a machine includes a drug delivery device, a graphic user interface, and a control unit in communication with the drug delivery device and the graphic user interface, the control unit being configured to display in a first region of the graphic user interface a multiple different screens relating to a blood processing treatment and in a second region of the graphic user interface a drug identifier that indicates a drug being administered by the drug delivery device, the control unit being configured so that when a drug is being administered by the drug delivery device, the drug identifier is displayed in the second region of the graphic user interface regardless of which of the different screens is being displayed in the first region of the graphic user interface.

Implementations can include one or more of the following features.

The control unit can be configured so that the second region of the graphic user interface includes a first color when the first drug is being administered such that a user can identify the drug based on the first color. The control unit can be configured so that the second region of the graphic user interface further displays text when the drug is being administered such that a user can identify the drug based on the text in the second region. The control unit can be configured so that the second region of the graphic user interface includes a second color that is different than the first color when the drug is not being administered such that a user can determine based on the second color that the drug is not being administered. The control unit can be configured so that the second region of the graphic user interface includes a second color that is different than the first color when a second drug is being administered such that a user can identify the second drug based on the second color.

In some implementations, the machine is a dialysis machine.

Implementations can have one or more of the following advantages. Using the systems and methods described herein, a dialysis machine user (e.g., a patient, a nurse, a clinician, or a similar machine operator) can determine what drug(s), if any, are being administered at a given time faster and easier than such determinations could be made using certain conventional dialysis systems. This advantage is achieved by always displaying, in a readily visible location and manner, a drug identifier when drug(s) are being administered. In some implementations, the drug identifier is color coded to allow the user to determine from afar what drugs are being administered.

Other aspects, features, and advantages will be apparent from the description and drawings, and from the claims.

DETAILED DESCRIPTION

This disclosure relates generally to dialysis drug delivery systems and related machines and methods. During dialysis treatments (e.g., hemodialysis treatments) various drugs can be administered to a patient using dialysis machines that include control panels having menus by which a user (e.g., a patient, nurse, clinician, or other dialysis machine operator) can operate the machine. In some cases, a visual indicator is displayed on the control panel during operation of the dialysis machine to convey information relating to which drugs are being administered at a given time. The visual indicator can include a text display and a color coding to indicate which drug(s), if any, are being administered at a given time during treatment. As a result, the user can readily determine drug delivery status when the user is near to or far from the dialysis machine. The systems and methods described herein of displaying the types of drugs being administered can provide the user with a quick and easy way to obtain the status of the dialysis treatment.

Figure 1:
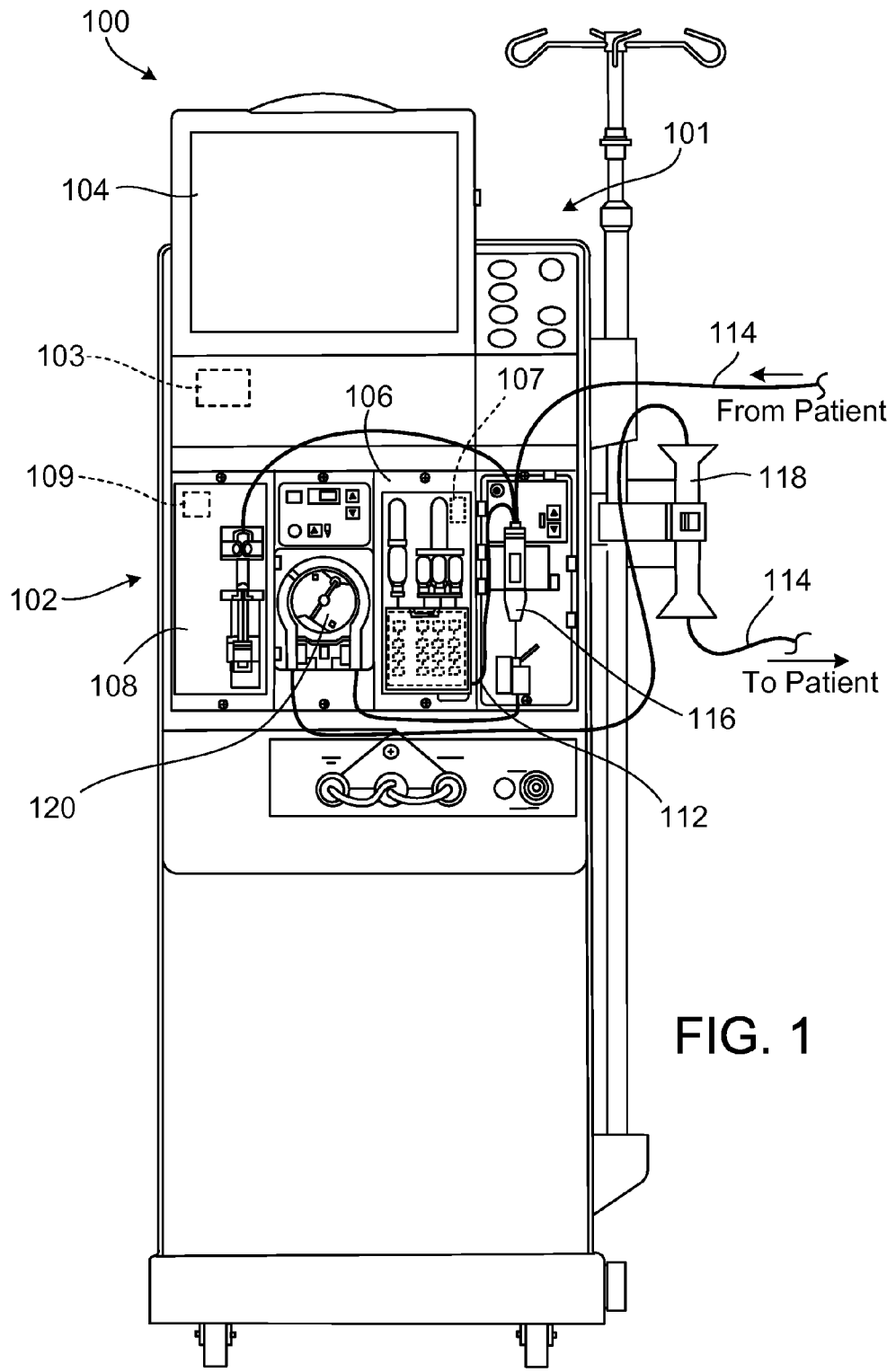
FIG. 1 is a schematic view of a hemodialysis machine that includes a modular drug delivery device and a modular heparin delivery device. A drug administration fluid line set and multiple drug vials are secured to the modular drug delivery device and the heparin delivery device.

Referring to FIG. 1, a hemodialysis system 100 includes a hemodialysis machine 101 that has a drug delivery system 102, a control unit (e.g., microprocessor) 103, and a control panel 104. The drug delivery system 102 includes a modular drug delivery device 106, a modular heparin delivery device 108, and a disposable drug administration fluid line set 110 that is connected to the drug delivery device 106 and the heparin delivery device 108. A drug delivery line 112 of the drug administration fluid line set 110 is fluidly connected to a blood circuit of the hemodialysis system 100. The blood circuit of the hemodialysis system 100 includes, among other things, a series of blood lines 114, a drip chamber 116, and a dialyzer 118. A blood pump (e.g., a peristaltic pump) 120 is configured to pump blood through the blood circuit during treatment. The hemodialysis system 100 also includes a dialysate circuit and various other components that, for the sake of simplicity, are not described in detail.

During hemodialysis treatment, blood is drawn from the patient and, after passing through the drip chamber 116, is pumped through the dialyzer 118 where toxins are removed from the blood and collected in dialysate passing through the dialyzer. The blood and dialysate are separated in the dialyzer by microporous tubes and flow in opposite directions. Toxins in the blood are transferred through the walls of the microporous tubes and are carried away in the dialysate. The cleansed blood is then returned to the patient, and the dialysate including the toxins (referred to as "spent dialysate") is disposed of or recycled and reused. As discussed in greater detail below, during the hemodialysis treatment, drugs (e.g., heparin, Epogen® and Venofer®) are delivered to the drip chamber 116 using the drug delivery system 102. The drugs mix with the patient's blood within the drip chamber 116 and are then delivered to the patient along with the patient's blood. The drip chamber 116 includes one or more inlet lines that can be temporarily secured to the drug delivery lines 112 to deliver drugs to the drip chamber 116. The drip chamber inlet lines include clamps that can clamp the inlet lines closed until they are connected to the drug delivery lines 112 and used to deliver drugs to the drip chamber.

Figure 2:
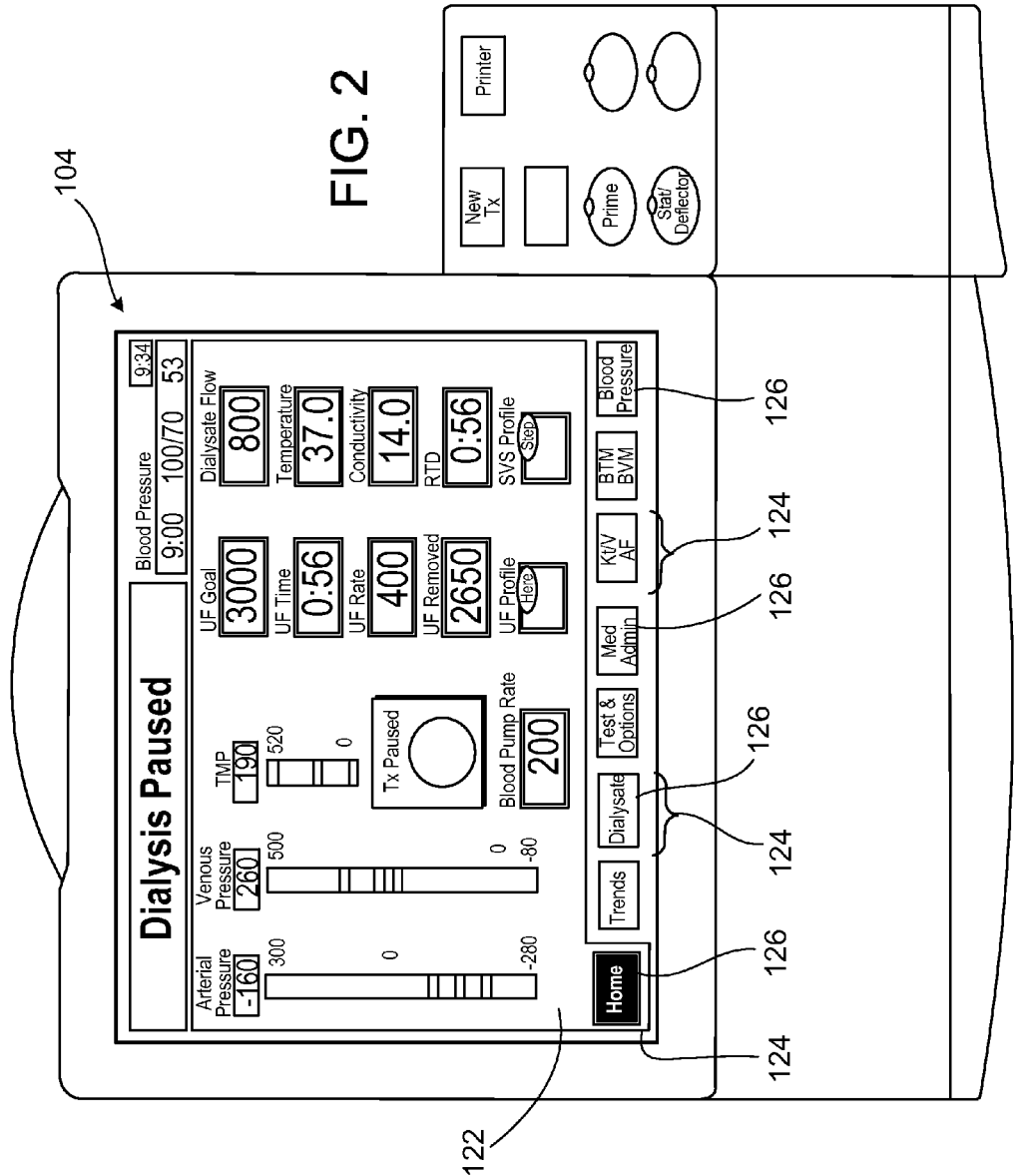
FIG. 2 is a schematic view of a control panel of the hemodialysis machine of FIG. 1.

Referring to FIG. 2, the control panel (e.g., a monitor to display multiple screens) 104 is used to operate the various components of the dialysis machine 101, including the blood pump 120 and the drug delivery system 102. The control panel 104 displays a series of selectable screens (e.g., menus) 122 in a first region of the control panel 104 that are used to set various treatment parameters and to monitor the treatment and patient status. For example, the control panel 104 includes menus 122 and corresponding selectable tabs 124 for selecting each of the different menus. The different menus include a Home menu, a Trends menu, a Dialysate menu, a Test & Options menu, a Medication Administration (Med Admin) menu, a Treatment Adequacy (Kt/V AF) menu, a Blood Temperature and Volume Monitoring (BTM/BVM) menu, and a Blood Pressure menu. Some menus 122 include additional sub-menus that appear upon selection of those menus. As described in greater detail below, for example, when a user selects the Med Amin menu, additional tabs, such as an Anemia Mgmt menu tab to select an Anemia Management menu and a Heparin menu tab to select a Heparin menu appear. The Anemia Management menu is used to set up, monitor, and control administration of certain drugs (e.g., Epogen® and Venofer®) that are given to the patient to manage anemia. The Heparin menu is used to set up, monitor, and control administration of heparin to the patient to prevent blood clotting, as discussed below. The control panel 104 is connected to the dialysis machine control unit 103 to monitor and control the various other systems and components of the dialysis machine 101.

During set up and operation of the hemodialysis system 100, the user can navigate the menus 122 to access, control, and monitor different aspects of the hemodialysis machine 101 by selecting or clicking on a portion (e.g., a tab indicator 126) of each tab 124. An input device (e.g., a keyboard, mouse, touchscreen, or similar device) of the control panel 104 is used to navigate the menus 122 and select the tab indicators 126. When a user selects a tab indicator 126, the tab indicator 126 changes appearance (e.g., changes color) to indicate the selection. For example, non-selected tab indicators can be displayed in one color (e.g., light blue) and when selected by the user, the tab indicator 126 can change to a different color (e.g., a darker blue).

As discussed below, in addition to changing color when selected, certain menu tab indicators 126 (e.g., the Med Admin tab indicator located in a second region of the control panel 104) change appearance to convey information relating to certain operations of the hemodialysis machine 101. For example, the Med Admin tab indicator 126 changes color to convey information relating to the drugs being administered by the dialysis machine 101. Additionally, the text displayed in the Med Admin tab indicator 126 can also change to describe the drugs (e.g., provide a drug name) being administered at a given time. When drugs are being delivered to the patient, the Med Admin tab indicator 126 conveys information relating to the drugs being delivered (e.g., by changing color and text) and is always displayed for the user regardless of which menu 122 the user is viewing.

Figure 3:
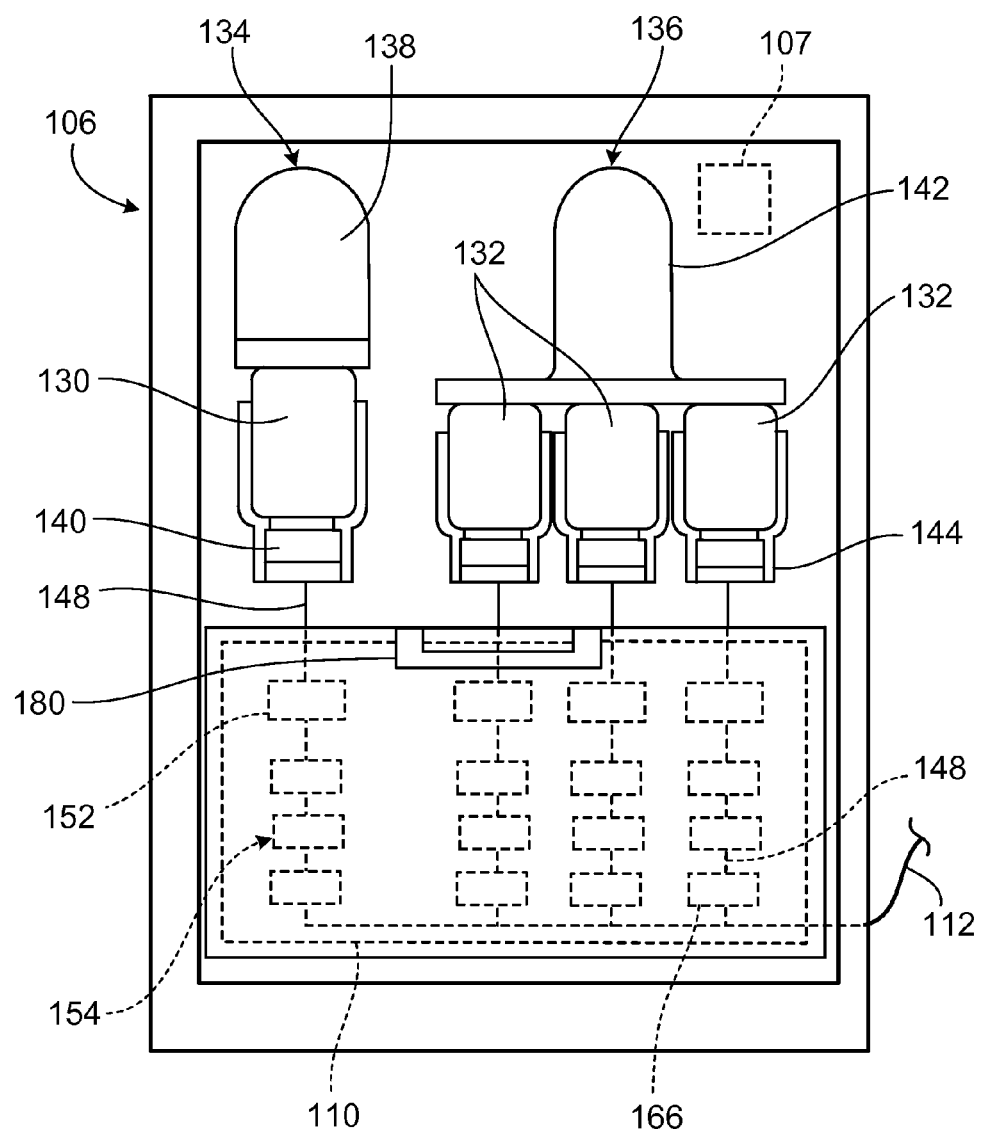
FIG. 3 is an enlarged schematic view of the drug delivery device and a portion of the drug administration fluid line set of FIG. 1.
Figure 4:
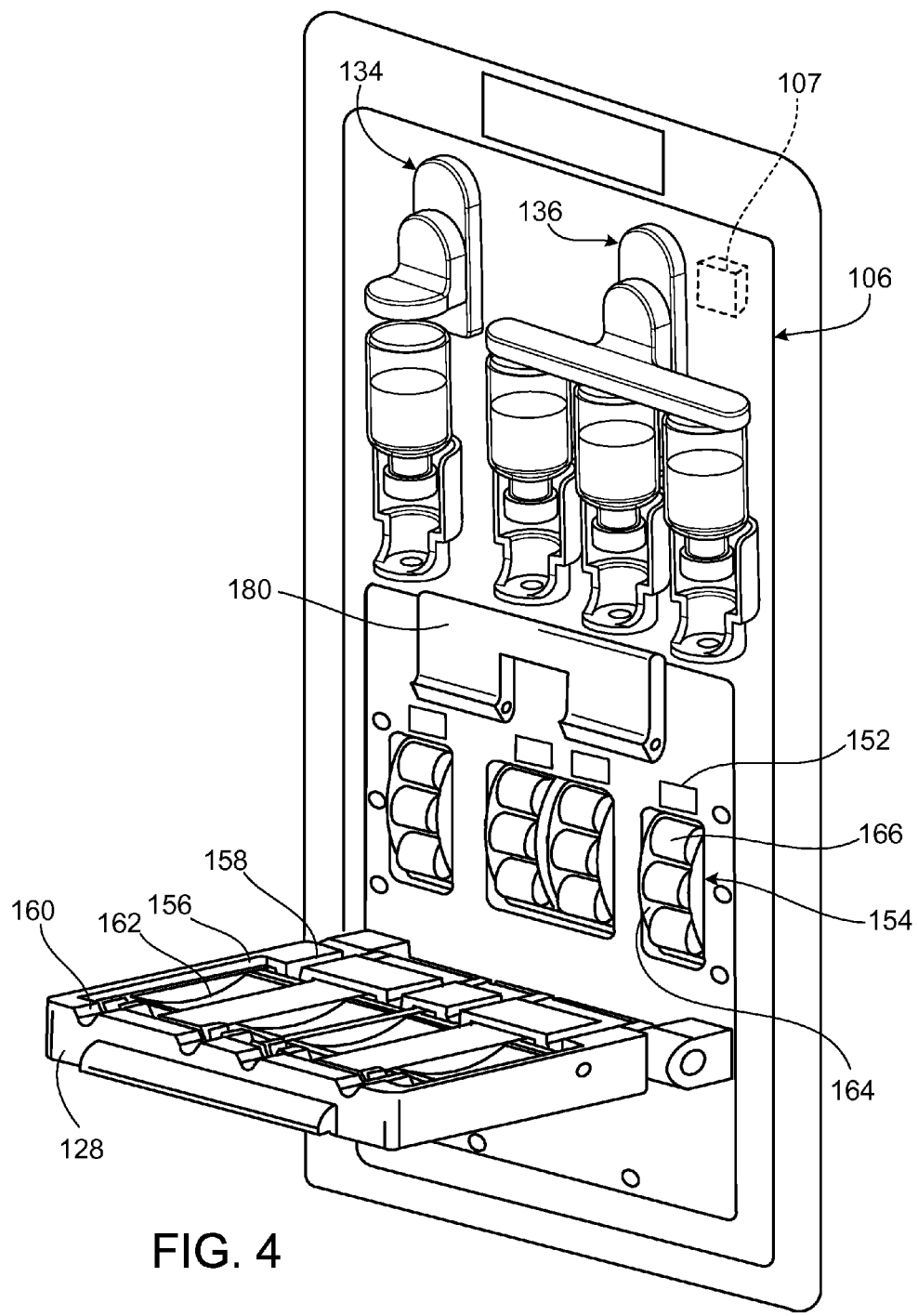
FIG. 4 is a perspective view of the drug delivery device of FIG. 3 with its door opened and the drug administration fluid line set removed to expose various components of the drug delivery device.

FIGS. 3 and 4 illustrate the drug delivery device 106 of the drug delivery system 102, which can be used to deliver drugs, such as Epogen® and Venofer®, to the drip chamber 116 of the blood circuit. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The modular drug delivery device 106 is attached to and exposed on the face of the hemodialysis machine 101, and, during use, a disposable drug administration fluid line set (also referred to herein as a drug administration fluid line cassette) 110 (shown in greater detail in FIG. 5) is disposed in a cassette compartment formed between a hinged door 128 and an inner face of the drug delivery device 106, as shown in FIG. 3. The drug administration fluid line set 110 is used to transport drugs from drug vials 130, 132 supported in drug vial holders 134, 136 to the drip chamber 116 of the blood circuit.

The drug vial holder 134 of the modular drug delivery device 106 is configured to hold a single Venofer® vial 130, and the drug vial holder 136 is configured to hold up to three Epogen® vials 132. The drug vial holder 134 includes a top member 138 and a bottom member 140 that can retain the single Venofer® vial 130 therebetween. The bottom member 140 has a top surface on which the cap of the inverted Venofer® vial 130 can rest. In certain implementations, the bottom member 140 includes a recess that is sized and shaped to receive a cap (or a portion of the cap) of the vial 130. This recess can help to ensure that the vial 130 is properly positioned in the vial holder 134. The bottom member 140 of the drug vial holder 134 also defines a through opening that allows an insertion portion of the drug administration fluid line set 110 to pass through the bottom member 140 and pierce a rubber seal of the Venofer® vial 130 during use.

The top and bottom members 138, 140 of the drug vial holder 134 are moveable relative to one another such that a drug vial can be compressed therebetween. In addition, the drug vial holder 134 as a whole is moveable in the vertical direction relative to the inner face of the drug delivery device 106 and relative to the insertion portion (e.g., a spike 146) of the drug administration fluid line set 110 when the line set 110 is disposed in the cassette compartment of the drug delivery device 106. As a result, when the line set 110 is disposed in the cassette compartment, the top and bottom members 138, 140 of the drug vial holder 134 can be moved in unison along with the Venofer® vial 130 to cause the spike 146 of the line set 110 to pierce the seal of the vial 130.

The drug vial holder 136, which holds the Epogen® vials 132 during use, is similar to the drug vial holder 134 described above. In particular, this drug vial holder 136 also includes top and bottom members 142, 144 between which three Epogen® vials 132 can be held, and the bottom member 144 defines three openings through which the spikes 146 of the line set 110 can pass to pierce the seals of the vials 132. In some implementations, the upper surface of the bottom member 144 defines recesses that receive the caps of the Epogen® vials 132 and help to ensure that the vials 132 are properly positioned in the vial holder 136. These recesses can, for example, help to ensure that the vials 132 are aligned with the openings in the bottom member 144 to allow the spikes 146 of the line set 110 to pierce the seals of the vials 132.

The drug vial holders 134, 136 of the drug delivery device 106 can be equipped with any of the various types of sensors described above for sensing the presence of a vial, identifying the type drug vial installed, detecting the size of the drug vials, and/or detecting the mass of the drug vials.

In certain implementations, for example, each drug vial holder 134, 136 includes a system that identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

Referring to FIGS. 1, 3, and 4, the sensors are connected to a drug delivery device control unit (e.g., microprocessor) 107 that is connected to the dialysis machine control unit 103. The drug delivery device control unit 107 can receive signals from and send signals to the various components of the drug delivery device 106, including, but not limited to, the drug vial ID sensors, bubble detectors 152, pumps 154, and other sensors along the drug lines in order to control and monitor drug delivery using the drug delivery device 106. The sensors provide drug-type information for the vials installed in each vial holder 134, 136 to the dialysis machine 101 and to the control panel 104 (e.g., via the drug delivery device control unit 107 connected to the dialysis machine control unit 103). Drug type information received from the sensors can be used to verify that vials 130, 132 are installed in the correct vial holders 134, 136 during machine set up. Verifying the correct vial location during machine setup allows the drug delivery device control unit 107 to later identify what drug(s), if any, are being administered at a given time by the drug delivery device 106.

Upon receiving signals from the drug vial ID sensors that do not match the inputted treatment information, an alarm (e.g., an audible and/or visual alarm) can be activated by the dialysis machine 101 or control panel 104. Alternatively or additionally, the drug delivery device 106 can be configured so that treatment cannot be initiated until the sensors detect the correct combination of vials.

Figure 5:
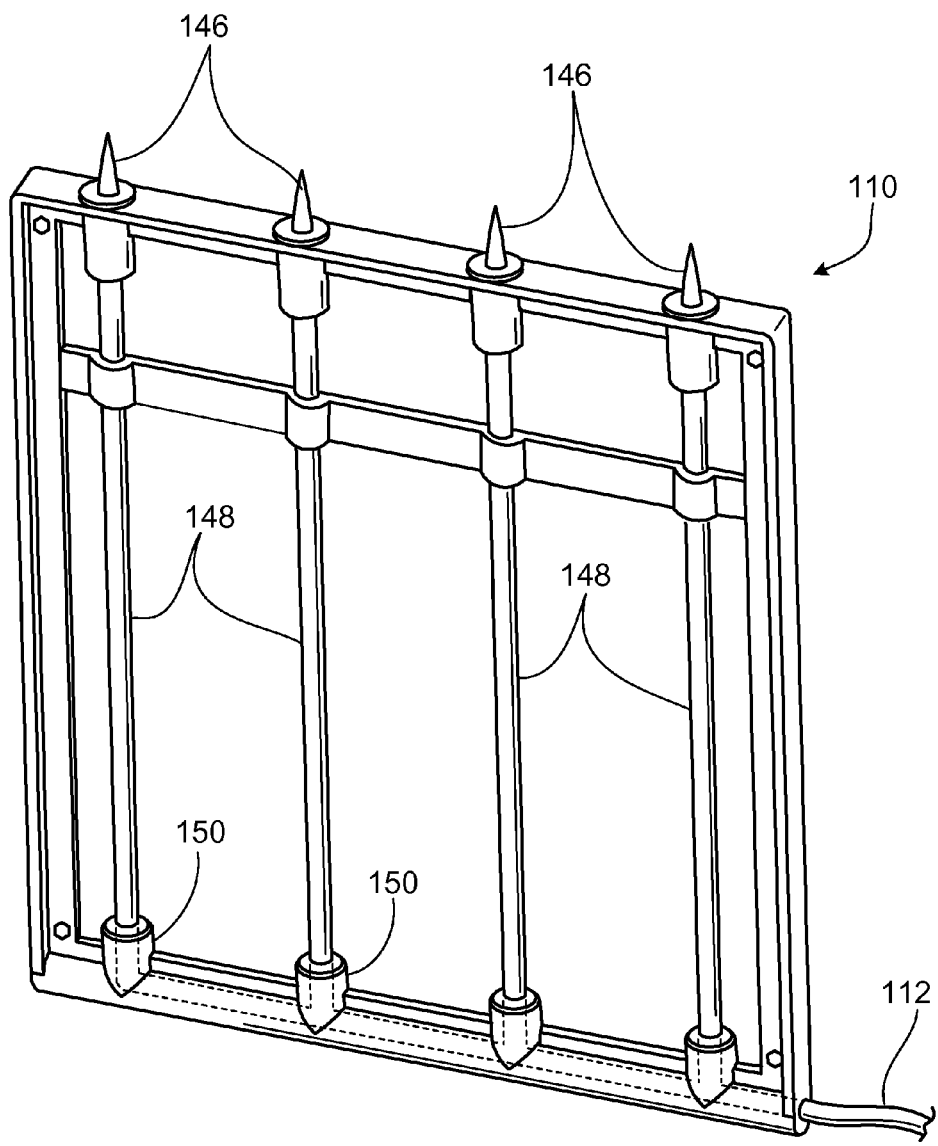
FIG. 5 is a perspective, exploded view of the drug administration fluid line set that is illustrated in dashed lines in FIG. 3.

The disposable drug administration fluid line set 110 is fluidly connected to each of the vials 130, 132. Referring to FIG. 5, the drug administration fluid line set 110 includes four drug vial connections (e.g., spikes 146) that connect to the vials 130, 132 in a manner to allow the drugs within the vials (i.e., the Venofer® 130 and Epogen® 132) to flow into feeder lines 148 via the drug vial spikes 146. Each of the feeder lines 148 is attached to a T-connector 150. The T-connectors 150 connect the feeder lines 148 to the drug delivery line 112. The drug vial spikes 146 can be formed of one or more relatively rigid medical grade plastics, such as polycarbonate or alpha-methylstyrene (AMS), and the various fluid lines can be formed of a more flexible medical grade plastic, such as polyvinylchloride (PVC).

Referring back to FIGS. 3 and 4, each of the feeder lines 148, passes by (e.g., is threaded through) a bubble detector 152. The bubble detectors 152 are capable of detecting air bubbles within the feeder lines 148. As a result, each of the bubble detectors 152 can determine whether its associated drug vial 130, 132 is empty during treatment, because air is drawn from the vial 130, 132 into the feeder line 148 when the vial is empty. The bubble detectors 152 are connected to the drug delivery device control unit 107 for monitoring flow of drugs to the patient and for properly priming the drug delivery line 112 during machine setup. As discussed below, signals from the bubble detectors 152 can be used by the drug delivery device control unit 107 to selectively operate the different pumps 154 as necessary and to provide signals to the control panel 104 to denote which drugs are being delivered. In some implementations, the bubble detectors 152 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 152 includes a sensor that, in addition to sensing the presence of an air bubble within its associated feeder line 148, can sense the presence of the feeder line itself. To accommodate the different feeder lines 148 associated with each vial 130, 132 and pump 154, the bubble detectors 128 are arranged in a spaced configuration across the inner face of the drug delivery device 103 to align with the vials 130, 132.

From the bubble detectors 152, each of the feeder lines 148 passes through (e.g., is threaded through) a peristaltic drug pump 154. As shown in FIG. 4, which illustrates the drug delivery device 106 with the door 128 opened and the drug administration fluid line set 110 removed, the inner surface of the door 128 includes a recessed region 156 that is configured to receive the line set 110 and elongate slots 158 that are configured to receive the feeder lines 148 of the line set 110 without substantially deforming the feeder lines 148. In certain implementations, the recessed region 156 and slots 158 are sized so that the line set 110 can be snapped into the recessed region 156 and slots 158, respectively, and thus releasably secured to the door 128. The inner surface of the door 128 can also include alignment features that are configured fit into the mating features formed in the line set 110 when the line set 110 is loaded into the door 128. The line set 110 can be sized and shaped to create a snap fit or a snug press fit into the door 128 during installation.

In addition, the inner surface of the door 128 defines recesses or raceways 162 that receive roller members 166 of the peristaltic pumps 154 of the drug delivery device 106 when the door 128 is closed. Springs are connected to top and bottom regions of each raceway 162 and to an internal fixed member in the door 128 to allow the raceway 162 to flex in response to contact with the rollers 166 of the peristaltic pumps 128 or in response to contact with the feeder lines 148 positioned between the raceways 162 and the rollers 166 of the peristaltic pumps 154.

Still referring to FIG. 4, the peristaltic pumps 154 are positioned in a spaced configuration across the face of the drug delivery device 106. Each peristaltic pump 154 includes a rotatable frame 164 and multiple rollers 166 rotatably positioned around the circumference of the frame 164. The peristaltic pumps 154 are configured to rotate about an axis that extends in a direction that is substantially parallel to the face of the drug delivery device 106. When the line set 110 is positioned in the cassette compartment between the inner face of the drug delivery device 106 and the closed door 128, the feeder lines 148 align with the pumps 154 and are thus pressed into the spring-loaded raceways 162 of the door 128. The spring force provided to the raceways 162 helps to take up tolerance between the raceways 162 and the rollers 166 and thus help to ensure that a fixed compression force is applied to the feeder lines 148 positioned between the raceways 162 and the rollers 166. During operation of the pumps 154, the rollers 166 are rotated from top to bottom (in the view show in FIG. 4) and thus force pillows or pockets of fluid downward through the associated feeder lines 148. This draws a vacuum on the associated vial 130, 132 causing drug to be drawn into the feeder lines 148 from the vials 130, 132.

The pumps 154 are connected (e.g., electrically connected) to the drug delivery device control unit 107 such that the drug delivery device control unit 107 can control and monitor the operation of each pump 154. For example, the control unit can control the pumps 154 to ensure that only one of the pumps 154 is pumping at a time. This helps to ensure that drug is pulled from only one of the vials 130, 132 at a time during treatment. The drug delivery device control unit 107 can control the timing at which the different pumps 154 are operated. For example, after the full contents of a vial have been evacuated, air will be sucked into the feeder line 148 associated with that vial. As the air passes through the feeder line 148, the bubble detector 152 will detect the air and transmit a signal to the drug delivery device control unit 107 indicating that the vial is empty. In response, the drug delivery device control unit 107 can stop the pumps 154 associated with the empty vial and start the pumps 154 associated with the vial containing the next drug to be delivered. The drug delivery device control unit 107 can also control the pumps 154 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon determining that the prescribed volume of the drug has been delivered (based on monitoring the operation of the pumps 154), the drug delivery device control unit 107 can turn off the pump 154 associated with that drug vial 130, 132 and turn on the pump 154 associated with the drug vial 130, 132 containing the next drug to be delivered. By monitoring the operation of each pump 154 and knowing which pumps 154 are delivering drugs to the drip chamber 116, the drug delivery device control unit 107 can determine what drug(s), if any, are being delivered in order to display the drug identifying information on the control panel 104.

The drug delivery device control unit 107 is configured to sense (e.g., by receiving signals from the dialysis machine control unit 103) if the blood pump 120 of the dialysis machine 101 is running and to pause drug delivery if the blood pump 120 is stopped. This technique prevents 'pooling' of the delivered drug in the drip chamber 116 during treatment.

The control panel 104 includes an Anemia Management (Anemia Mgmt) menu (shown in FIGS. 10-14) that is used to control and monitor the delivery of the anemia management drugs (e.g., Epogen® and Venofer®) during treatment. Information input to the Anemia Mgmt menu 122 on the control panel 104 can include prescribed dosages of Epogen® and Venofer®. Based on the information input to the Anemia Mgmt menu 122, the drug delivery device control unit 107 can control the operations of the pumps 154 to administer the appropriate drugs in an automatic and controlled manner.

Figure 6:
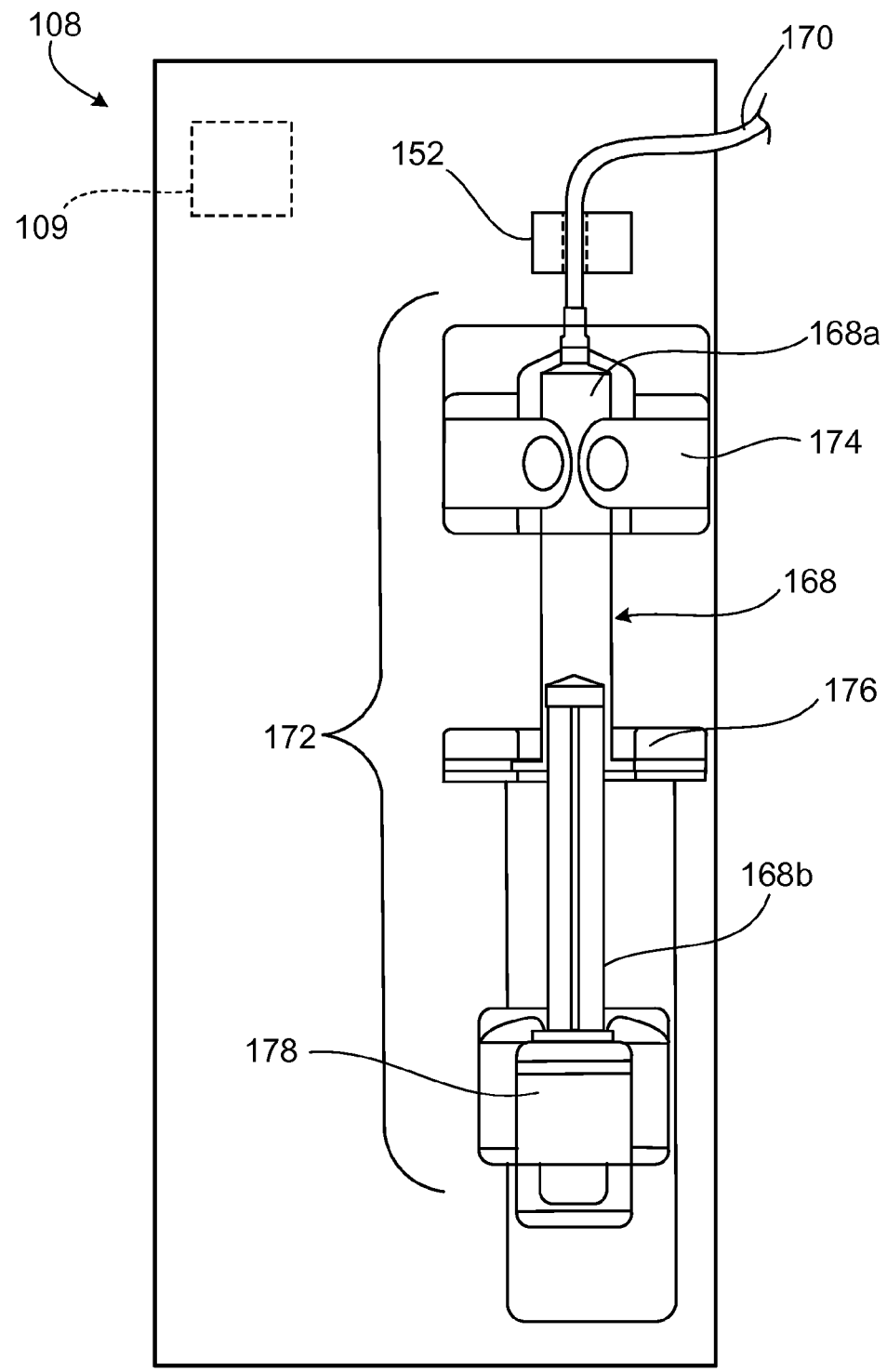
FIG. 6 is an enlarged schematic view of the heparin delivery device of the hemodialysis machine of FIG. 1.

In addition to withdrawing drugs from vials using the modular drug delivery device 106, the drug delivery system 102 includes the modular heparin delivery device 108, which injects heparin from a syringe 168 into the hemodialysis blood circuit via a heparin delivery line 170. Injection can occur gradually over the course of the hemodialysis treatment or as a bolus dosage. Referring to FIG. 6, the heparin delivery device 108 includes a syringe holder 172 to secure and operate the syringe 168 during treatments. The syringe holder 172 includes barrel lock tabs 174 to secure the syringe barrel 168a and a slot 176 to hold wings of the syringe barrel 168a to prevent the syringe barrel 168a from moving vertically. The syringe holder 172 also includes a slide carriage 178 that secures an outer end of the syringe plunger 168b and is vertically moveable to depress the syringe plunger 168b into the syringe barrel 168a and expel heparin from the syringe 168. The syringe holder 172 is sized to accommodate a variety of commercially available syringe sizes. For example, the syringe holder 172 can accommodate 10-12 ml disposable syringes.

The heparin delivery device 108 is connected to a heparin delivery device control unit (e.g., microprocessor) 109 that is connected to the dialysis machine control unit 103. The heparin delivery device control unit 109 can control the timing and rate at which the heparin delivery device 108 delivers heparin to the patient. Typically, the heparin delivery device control unit 109 controls heparin delivery by controlling the position and motion of the slide carriage 178 during treatments. The heparin delivery device control unit 109 also sends signals to the dialysis machine control unit 103 when the heparin delivery device 108 is delivering heparin to the patient so that the control panel 104 can display the appropriate drug delivery information (e.g., on the Med Admin tab indicator 126).

Like the drug delivery device control unit 107, the heparin delivery device control unit 109 is configured to sense if the blood pump 120 of the dialysis machine 101 is running and to pause heparin delivery if the blood pump 120 is stopped. This technique prevents 'pooling' of the heparin in the drip chamber 116 during treatment.

As discussed above, the control panel 104 includes a Heparin menu (shown in FIGS. 8 and 9) that is used to control and monitor the amount of heparin administered during treatment and the rate of administration. Information input to the Heparin menu 122 on the control panel 104 can include a type of syringe (e.g., a syringe manufacturer and size) used to administer heparin, a heparin delivery rate, infusion time, and bolus dose (if administered during treatment). Based on the information input to the Heparin menu 122, the heparin delivery device control unit 109 can control the motion of the slide carriage 178 to administer heparin to patient in an automatic and controlled manner.

During treatment, the slide carriage 178 is automatically moved toward the syringe holder barrel lock 174 to administer heparin to a patient as necessary based on the prescribed dosage. As the slide carriage 178 forces the syringe plunger 168b into the syringe barrel 168a, heparin flows from the syringe 168 through the heparin delivery line 170 and is delivered to the drip chamber 116. From the drip chamber 116, the heparin flows onto the blood lines 114 of the hemodialysis system 100. When installed, the heparin delivery line 170 passes by (e.g., is threaded through) a bubble detector 152 that is used monitor heparin flowing to the drip chamber 116. The bubble detector 152 is also connected to the heparin delivery device control unit 109 for monitoring the heparin being delivered to the patient. For most treatments, the slide carriage 178 is configured to move the syringe plunger 168b relative to the syringe barrel 168a in order to administer heparin in a variety of dosage rates (e.g., 0 to 9.9 ml/hr).

During hemodialysis treatments, the drug delivery device control unit 107 and the heparin delivery device control unit 109 continuously communicate with the dialysis machine control unit 103 to provide signals so that the control panel 104 can continuously display (e.g., on the Med Admin tab indicator) what drugs, if any, are being delivered to the patient by the drug delivery device 106 and the heparin delivery device 108.

Machine Setup and Treatment

Prior to beginning a hemodialysis treatment, the various lines and passages that make up the blood circuit and dialysate circuit of the hemodialysis machine 101 are primed, the patient lines 105 are connected to the patient, and the hemodialysis machine 101 is programmed for treatment.

Figure 7:
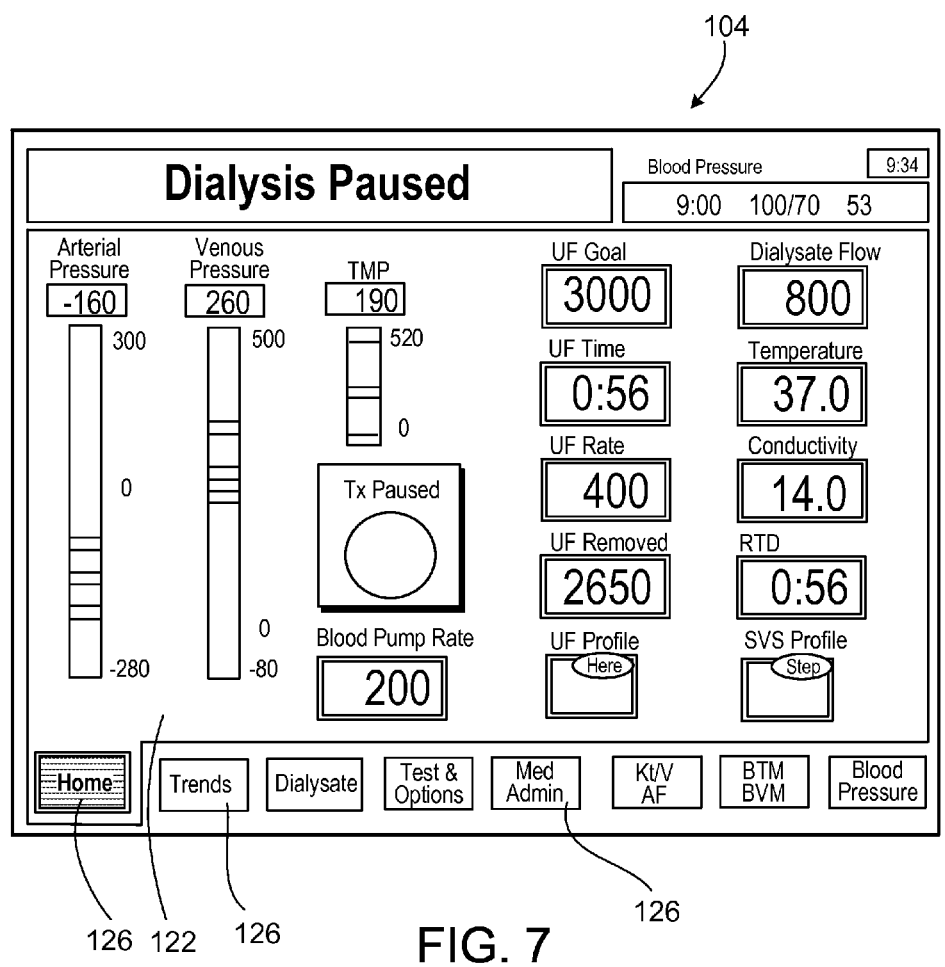
FIG. 7 illustrates a Home menu displayed on the control panel of the hemodialysis machine of FIG. 1.

Referring to FIG. 7, to program the machine 101 for treatment, a user accesses the control panel 104 and navigates to various treatment setup menus 122, including the Home menu and the Dialysate menu. While various menus 122 are used to program many different parameters (e.g., an ultrafiltration goal input at the Home menu, an ultrafiltration profile input at the Home menu, a concentration type input at the Dialysate menu, prescribed Base Na+ and bicarbonate values input at Dialysate menu) used for dialysis treatment, much of the machine and treatment set up, for simplicity, is not specifically discussed. Once the dialysis treatment parameters are input in the appropriate menus 122, the user navigates to the Home menu 122 to begin the dialysis treatment.

As shown in FIG. 7, during treatment set up, the Med Admin tab indicator 126, which is always displayed during treatment, is displayed along the bottom of the control panel 104. Since no drugs are being delivered to the patient, the Med Admin tab indicator 126 is displayed in its standard appearance (e.g., light blue) while the user navigates the Home menu 122 to begin treatment. The Med Admin tab indicator 126 is also always displayed while the user navigates other menus 122 (e.g., the Dialysate menu, the Trends menu, or other menus) during setup or during dialysis treatment.

After inputting all necessary dialysis parameters, the user can start the dialysis treatment by selecting the Tx Paused button on the Home menu 122 to begin circulating blood and dialysate throughout the respective fluid circuits. In some cases, due to machine setup, blood or dialysate will already be circulating through their respective fluid circuits when the user selects the Tx Paused button. Once the dialysis treatment begins (i.e., once both blood and dialysate are flowing through their respective circuits) the user can set up the various drug delivery lines to administer drugs (e.g., heparin, Venofer®, and Epogen®) during the treatment. Alternatively, the user can set up the drug delivery devices prior to starting dialysis treatment.

Since heparin is typically delivered to a patient before the Venofer® or Epogen® during dialysis treatment, the heparin delivery device 108 (shown in FIG. 6) is typically set up and programmed shortly after dialysis treatment begins. First, a heparin syringe 168 is installed onto the heparin delivery device 108 using the syringe holder 172. Once installed, the heparin delivery line 170 is connected to one of the drip chamber inlet lines and the clamp for that inlet line is removed to create a fluid connection between the syringe 168 and the drip chamber 116.

Figure 8:
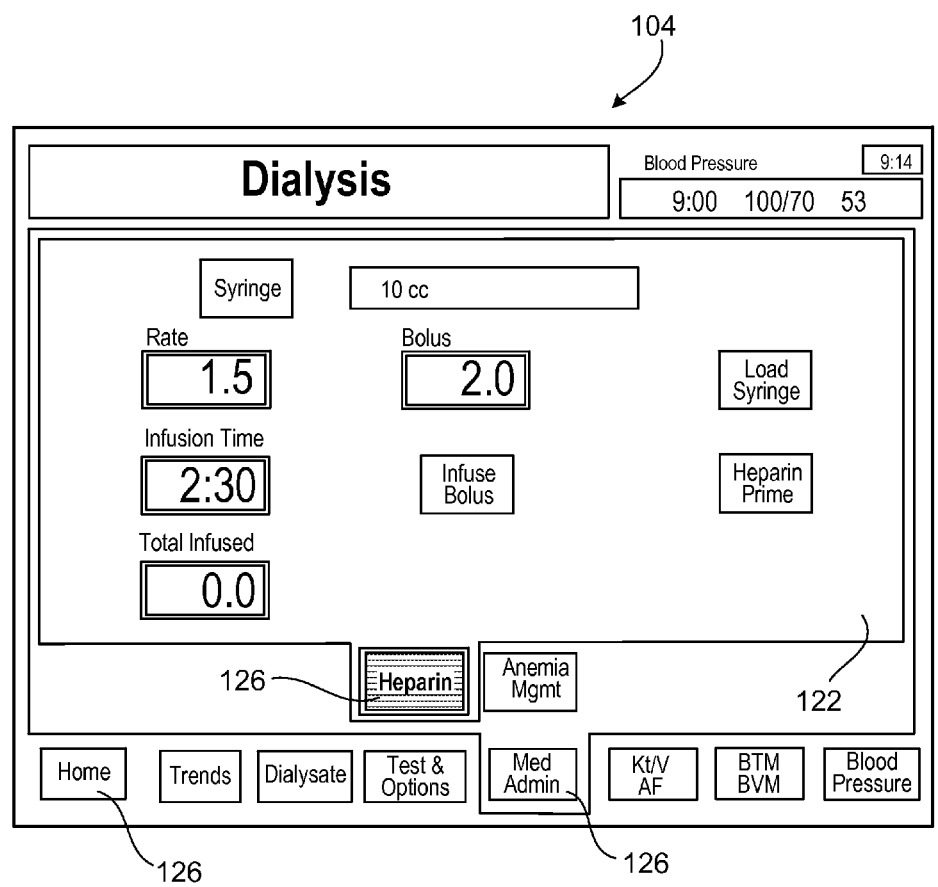
FIG. 8 illustrates a Heparin menu displayed on the control panel of the hemodialysis machine of FIG. 1 to set up heparin delivery during hemodialysis treatment.

Referring to FIG. 8, once the syringe 168 and the heparin delivery line 170 are installed, the user can input syringe information into the Heparin menu 122 so that the heparin delivery device 108 can properly prime the heparin feeder line 170. To access the Heparin menu 122 on the control panel 104, the user selects the Med Admin tab indicator 126 which typically presents the Heparin menu 122 by default. If the Heparin menu 122 is not presented by default, the user can select the Heparin tab indicator 126. The Heparin tab indicator 126 is displayed as either light blue (e.g., when not selected) or dark blue (e.g., when selected to present the Heparin menu). To input syringe information, the user selects the Syringe button on the Heparin menu 122 and selects the appropriate syringe type from a drop-down menu. As shown, when the user is setting up heparin delivery, the Med Admin tab indicator 126 remains blue (i.e., light blue because the Heparin menu is selected) and displays "Med Admin" because no drugs are yet being delivered to the patient. Once all of the necessary syringe information is entered, the user can enter the prescribed dosage information (e.g., the infusion rate, or a bolus dose amount) and select the Heparin Prime button and confirm the information to begin priming the heparin delivery line 170.

Priming can be an automated process that begins after the operator confirms that the heparin syringe 168 has been loaded and the prescribed dose information is correct. To prime the heparin delivery line 170, the slide carriage 178 is activated to expel heparin from the syringe 168 of the heparin delivery device 108 to the drip chamber 116. From the syringe 168, heparin passes by the bubble detector 152 in the heparin delivery line 170 and then continues for a predetermined amount of time after the heparin is detected by the bubble detector 152. The slide carriage 178 continues to operate for a sufficient period of time to cause the heparin to substantially fill the heparin delivery line 170, which primes the heparin delivery line 170. Priming the heparin delivery line 170 helps to ensure that as additional heparin is expelled from the syringe 168 into the heparin delivery line 170, an approximately equal amount of heparin enters the drip chamber 116. Once the heparin delivery line 170 is primed, the slide carriage 178 temporarily stops moving to stop forcing heparin from the syringe 168.

If heparin is not detected by the air bubble detectors 152 during the priming process, an alarm is activated. This typically indicates a problem with either the heparin delivery device 108 (e.g., the bubble detector 152 of the heparin delivery device 108) or the drug administration fluid line set 110 (e.g., the syringe 168 or heparin delivery line 170). In response to the alarm, the user typically replaces the drug administration fluid line set 110 or adjusts the drug administration fluid line set 110 and repeats the process.

Once the heparin delivery device 108 is set up and primed, delivery of heparin typically begins automatically as long as the blood pump 120 is operating. Alternatively, a Start button can appear on the Heparin menu 122 after priming is complete that begins heparin delivery when selected. As the slide carriage 178 starts moving and forces the plunger 168*b* into the barrel 168*a* and heparin enters the drip chamber 116, the dialysis machine control unit 103 determines that heparin is being delivered (e.g., by receiving a signal from the heparin delivery device control unit 109).

Figure 9:
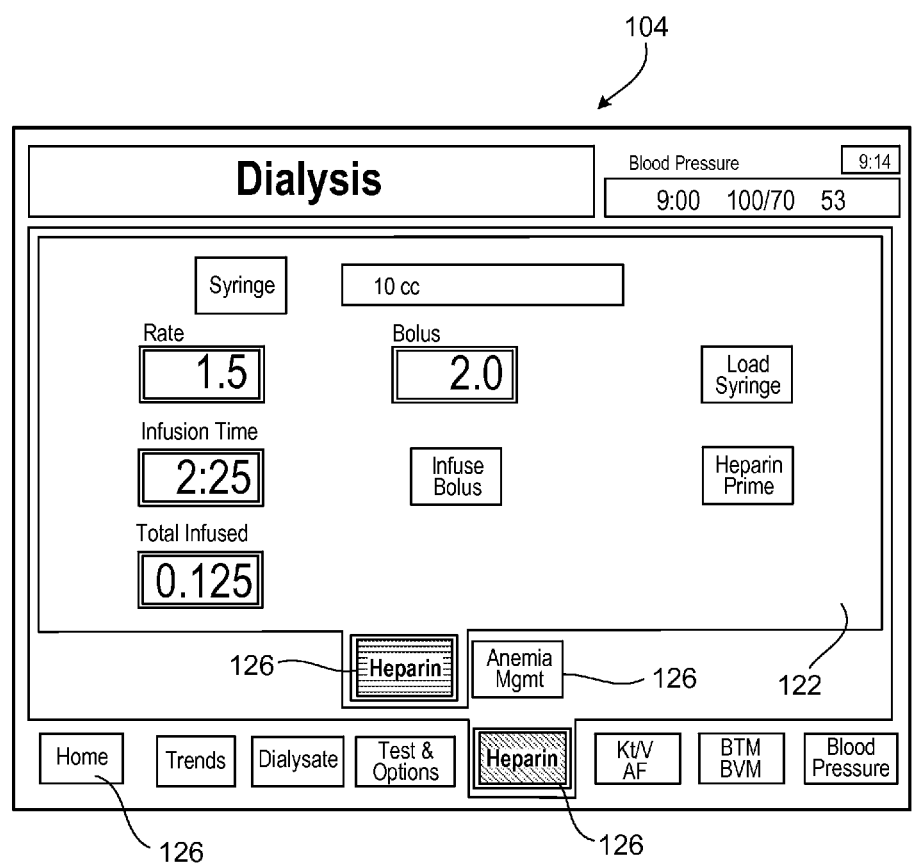
FIG. 9 illustrates the Heparin menu of FIG. 8 while heparin is being delivered to a patient during hemodialysis treatment.

Referring to FIG. 9, when heparin is being delivered to the patient, the Med Admin tab indicator 126 changes color from light blue to green and the text displayed on the tab indicator 126 changes from "Med Admin" to "Heparin" to indicate that heparin is being delivered. While heparin is being delivered, the altered Med Admin tab indicator 126 (i.e., the green Heparin tab indicator) always remains displayed, even while the user navigates other menus during treatment.

Typically, the user will set up the drug delivery device 106 and associated lines in order to deliver Venofer® and Epogen® to the patient after setting up the heparin delivery device 108. For example, the drug delivery device 106 can be set up while heparin is being delivered to the patient. To set up the drug delivery device 106, the Venofer® and Epogen® vials 130, 132 are loaded into the respective vial holders 134, 136. As discussed above, sensors in the drug delivery device 106 can verify that the correct vials are installed in the appropriate vial holders. To set up the drug delivery lines, the user connects the disposable drug administration fluid line set 110 (e.g., the feeder lines 148) to the inner surface of the door 128. Typically, alignment features of the line set 110 and the door 128 help ensure that the correct line set 110 remains properly secured fixed to the door 128. For example, drug administration fluid line sets that do not include correct mating features that correspond to mating features of the door 128 could not be properly secured to the door 128. This would indicate to the operator that an incorrect line set 110 was loaded into the cassette compartment of the drug delivery device 106 and, in many cases, would prevent the door 128 from shutting and thus prevent the drug delivery device 106 from being operated with that line set.

After loading the drug administration fluid line set 110 onto the door 128, the operator closes the door 128 and secures a latch 180 to hold the door 128 in the closed position. Because the line set 110 is securely fastened to the door 128 in a desired position, the feeder lines 148 align with their associated pumps 154 and bubble detectors 152 when the door 128 is closed. Thus, as the door 128 is closed, the protruding peristaltic pumps 154 press the feeder lines 148 into the raceways 162 formed along the inner surface of the door 128, and the inner surface of the door 128 presses the feeder lines 148 into engagement with the bubble detectors 152. With the door 128 in the closed position, the spikes 146 of the line set 110 rest directly below the holes formed in the bottom members 140, 144 of the vial holder 134, 136. Once the line set 110 is properly positioned and the door 128 is closed, the drug delivery line 112 is connected to one of the drip chamber inlet lines and the clamp on that inlet line is removed to create a fluid connection between the line set 110 and the drip chamber 116.

Figure 10:
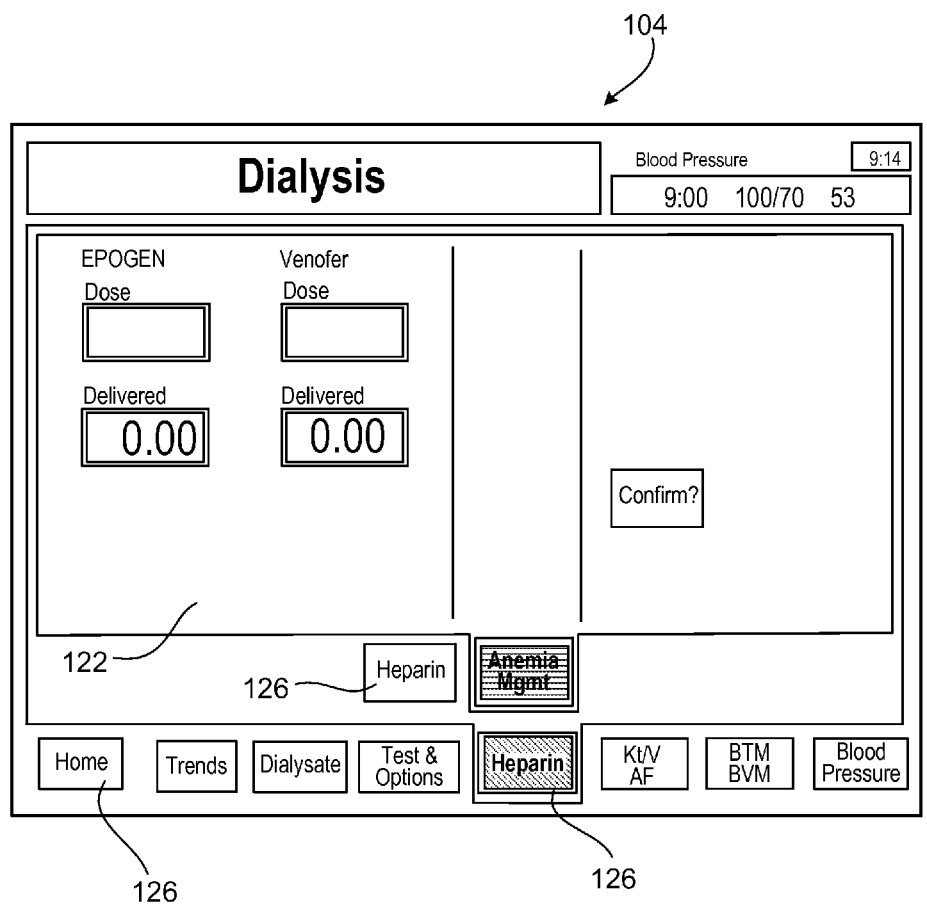
FIG. 10 illustrates an Anemia Management menu displayed on the control panel of the hemodialysis machine of FIG. 1 to set up delivery of drugs used for anemia management during hemodialysis treatment.

With the line set 110 installed, the user enters the prescribed dosages of Venofer® and Epogen® into the control panel 104 of the dialysis machine 101. To enter or select the prescribed dosages, the user navigates to the Anemia Management (Anemia Mgmt) menu 122 by selecting the Med Admin tab indicator 126 (if not already selected) and then the Anemia Mgmt tab indicator 126. Like the other tab indicators 126, the Anemia Mgmt tab indicator 126 is displayed as either light blue (e.g., when not selected) or dark blue (e.g., when selected to present the Anemia Mgmt menu). As shown in FIG. 10, since heparin is being delivered, while the user navigates the Anemia Mgmt menu 122 to setup Venofer® and Epogen® delivery, the Med Admin tab indicator 126 is green and displays, "Heparin." The user selects the respective Dose buttons and enters the prescribed dosage of each drug (e.g., by selecting the dosages from a drop-down menu or by keying in the dosage amount). The user, after reviewing the prescribed dosages entered into the control panel 104, confirms that the prescribed dosages are correct by pressing a button (e.g., an "Accept" or "Confirm" button) that appears on the Anemia Mgmt menu 122 or the drug delivery device 106 after dosages are entered. Upon confirmation of the prescribed dosages, the vial sensors confirm that the correct drug vials are installed in the correct locations. With the correct vial installation confirmed, the drug delivery device 106 can later determine what drug is being delivered based on which drug pump 154 is operating.

The user then presses a button (e.g., an additional "Confirm" button that appears on the Anemia Mgmt menu 122 or that is present on the drug delivery device 106) to confirm that the line set 110 is installed and the clamps on the drip chamber inlet lines are open. This confirmation presents a Start button on the Anemia Mgmt menu 122 that, upon selection, initiates spiking the drug vials and priming the feeder lines 148 and the drug delivery line 112. Once the lines are primed, delivery of the drugs will typically begin automatically, therefore, confirmation can be delayed if the user desires delivery of the drugs at a later point in the dialysis treatment.

To prime the feeder lines 148, the drug pumps 154 are sequentially activated for a predetermined time after the drug from their associated vials are detected by their respective bubble detectors 152. After detection of the drug by the air bubble detector 152 associated with each Epogen® vial 132 (i.e., the first vial that is to be emptied during the drug delivery process), the drug pumps 154 continue to operate for a sufficient period of time to cause the Epogen® to substantially fill the drug delivery line 112. Substantially filling the feeder line with the Epogen® ensures that as additional Epogen® is drawn from the vial 132, a substantially equal amount of Epogen® will enter the drip chamber 116. If the drug is not detected by the respective air bubble detector 152 during the priming process, the drug delivery device 106 recognizes a problem with either the drug delivery device 106 (e.g., the bubble detector 152 of the drug delivery device 106) or the drug administration fluid line set 110 (e.g., the drug vial spike 146 or feeder line 148 of the drug administration fluid line set 110). In response to recognizing the problem, the drug delivery device 106 will typically move on and attempt to prime the next feeder line 148 for drug delivery.

Drug delivery typically begins automatically after priming the feeder lines 148 and the drug delivery line 112 as long as blood is being pumped through the blood circuit (i.e., as long as the blood pump 120 is operating). While the delivery sequence can vary based on a particular patient or delivery site, in this example, Epogen® is delivered to the patient first. Epogen® is delivered from the Epogen® vial 132 to the drip chamber 116 where it mixes with the patient's blood. The Epogen® is delivered to the patient by operating the pump 154 associated with the Epogen® vial 130 (while leaving all of the other pumps 154 stationary). The volume of Epogen® delivered to the patient is monitored and controlled by the drug delivery device control unit 107 by controlling the respective drug pumps 154 of the drug delivery device 106.

Figure 11:
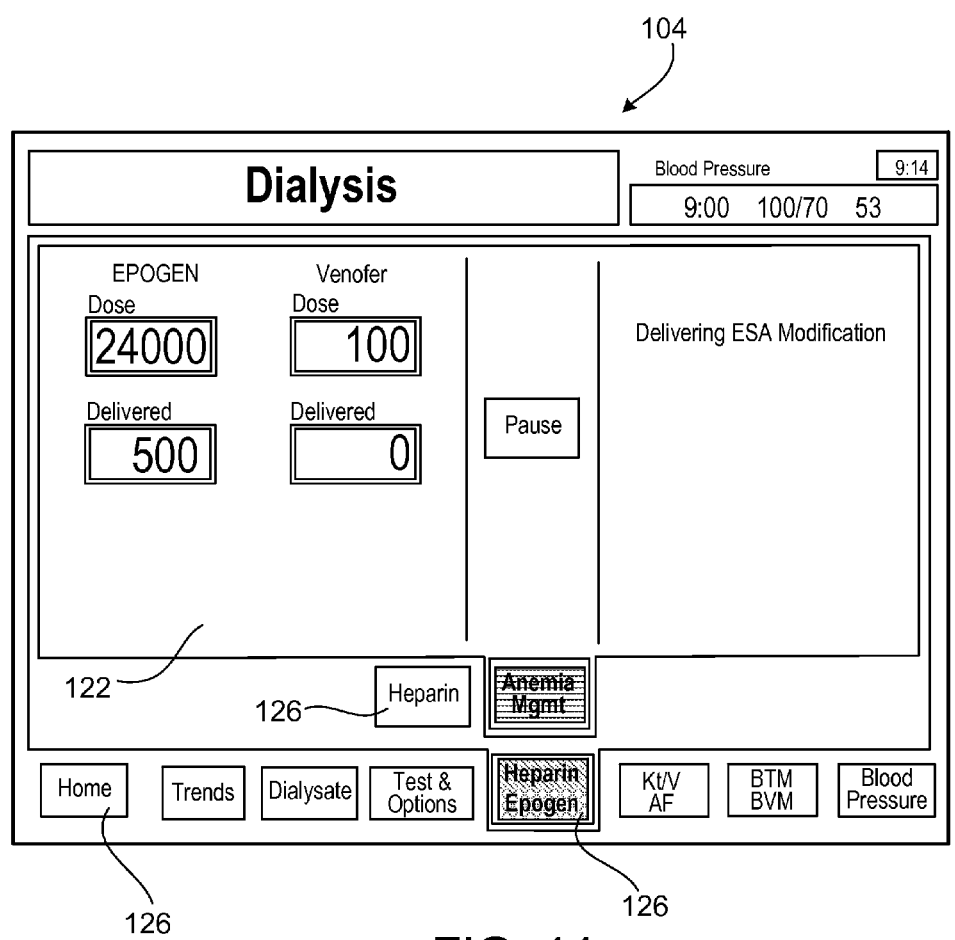
FIG. 11 illustrates the Anemia Management menu of FIG. 10 while heparin and Epogen® are being delivered to the patient during hemodialysis treatment.

During drug delivery, when one of the drug pumps 154 is running, the drug delivery device control unit 107 sends a signal to the dialysis machine control unit 103 to indicate which drug is being delivered. Referring to FIG. 11, when the delivery of Epogen® begins, the appearance of the Med Admin tab indicator 126 changes to reflect that Epogen® is being delivered. Since heparin is also being delivered, once the drug pump 154 begins pumping Epogen® into the drip chamber, the Med Admin tab indicator 126 changes from being all green and displaying "Heparin" to being colored in two regions (e.g., an upper region and a lower region). The upper region is green and displays "Heparin" and the lower region is yellow and displays "Epogen" to denote that both heparin and Epogen® are being delivered to the patient. If the prescribed dosage of heparin is fully delivered before delivery of the Epogen® begins, then upon delivery of the Epogen®, the Med Admin tab indicator 126 would indicate that only the Epogen® is being delivered by turning all yellow and displaying "Epogen." If the prescribed dosage of Epogen® is greater than the volume of the first Epogen® vial 130, the next feeder line 148 (e.g., an adjacent feeder line 148) is primed after all of the Epogen® is delivered from the first Epogen® vial 130. Priming of the subsequent feeder lines 148 occurs in the same manner described above with the first feeder line 148 and delivery of the Epogen® begins automatically after priming.

Figure 12:
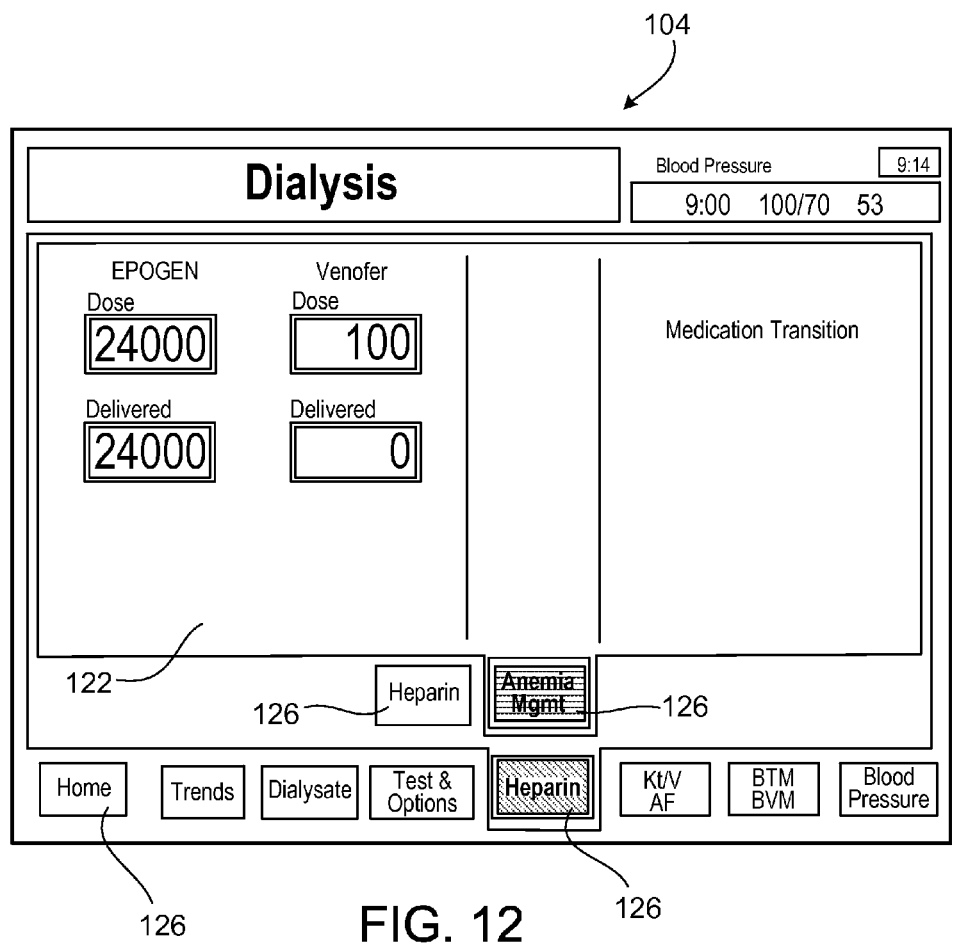
FIG. 12 illustrates the Anemia Management menu of FIG. 10 after Epogen® delivery has been completed.

Referring to FIG. 12, when Epogen® is no longer being delivered (i.e., when the entire Epogen® dosage is complete) and heparin is still being delivered, the Med Admin tab indicator 126 returns to being completely green and displaying "Heparin" to indicate that delivery of Epogen® has stopped and only heparin is being delivered. If, however, heparin delivery is also complete when Epogen® delivery ends, the Med Admin tab indicator 126 will return to blue (e.g., dark blue if selected and light blue if another menu is selected) and display "Med Admin" to denote that no drugs are being delivered.

Once the entire dosage of Epogen® 15 delivered, the drug delivery is typically paused briefly before Venofer® delivery begins. A medication transition pause between the delivery of Epogen® and Venofer® gives the blood circuit adequate time to flush Epogen® from the drip chamber 116 to avoid mixing Epogen® and Venofer® in the drip chamber 116. The duration of the medication transition pause can vary based on the size of the drip chamber 116. For example, relatively large drip chambers will typically require a longer medication transition pause time than a smaller drip chamber.

Figure 13:
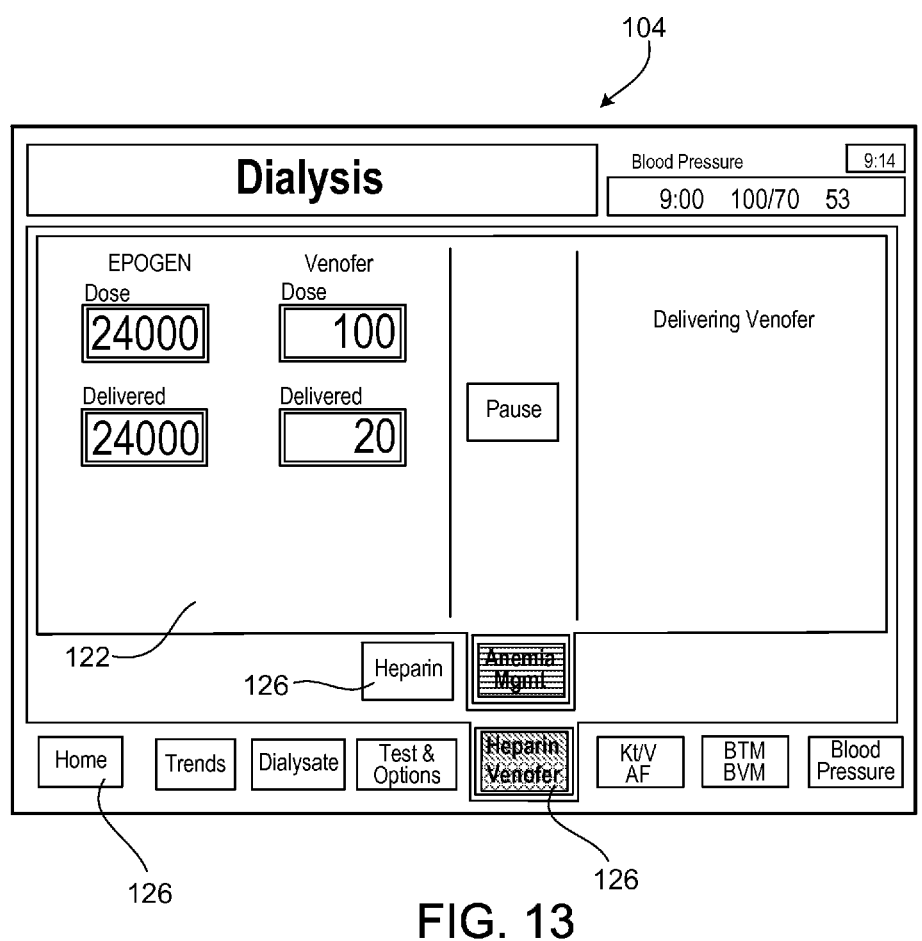
FIG. 13 illustrates the Anemia Management menu of FIG. 10 while heparin and Venofer® are being delivered to the patient during hemodialysis treatment.

After the medication transition pause is complete, the Venofer® feeder line 148 is primed in the same manner as the Epogen® feeder lines (discussed above). Once primed, delivery of Venofer® begins automatically as long as the blood pump 120 is running Referring to FIG. 13, once the drug delivery device 106 begins delivering Venofer® to the drip chamber 116, the appearance of the Med Admin tab indicator 126 changes to describe the drug(s) being delivered. In FIG. 13, the Med Admin tab indicator 126 is colored in two regions (e.g., an upper region and a lower region). The upper region is green and displays "Heparin" and the lower region is yellow and displays "Venofer" to denote that heparin and Venofer® are being administered to the patient. As with the delivery of Epogen®, if Venofer® delivery begins after the entire dosage of heparin has been delivered or if the delivery of heparin finishes during Venofer® delivery, the Med Admin tab indicator 126 would change to all yellow and display only "Venofer" to indicate that only Venofer® is being delivered.

Figure 14:
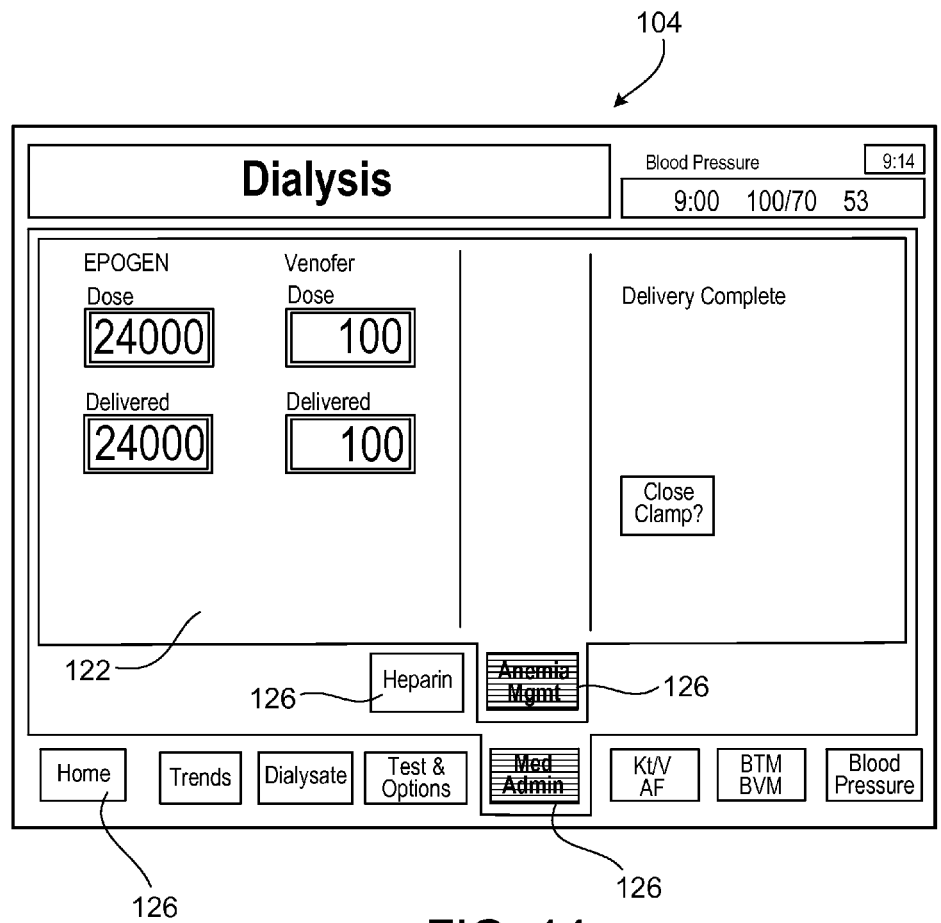
FIG. 14 illustrates the Anemia Management menu of FIG. 10 after heparin and Venofer® delivery has been completed.

After the prescribed dosage of Venofer® is delivered, the Med Admin tab indicator 126 again changes to indicate what drug(s) is/are being delivered. If heparin is still being delivered upon completion of the Venofer® delivery, the Med Admin tab indicator 126 becomes all green and displays "Heparin." Instead, if the entire dosage of heparin has been delivered by the time that Venofer® delivery is complete, as shown in FIG. 14, the Med Admin tab indicator 126 returns to its standard, blue appearance (i.e., dark blue if selected and light blue if another tab indicator 126 is selected), indicating the no drugs are being delivered. Once all drugs have been delivered, the Anemia Mgmt menu 122 will prompt the user to close the clamps on the drip chamber inlet lines and dialysis treatment can resume as desired.

While these different configurations of the Med Admin tab indicator 126 have been shown and described with respect to the Heparin menu 122 and the Anemia Mgmt menu 122, the changes in appearance of the Med Admin tab indicator 126 occur in the same manner while the user views any of the other control panel menus 122 (e.g., the Home menu or the Dialysate menu). In particular, regardless of the menu 122 that is selected, the Med Admin tab indicator 126 will be colored and provided with text to indicate what drug(s), if any, is/are being delivered. The constant display of the Med Admin tab indicator 126 along with the color coding and text allows the user to readily determine which drug(s) is/are being delivered from far around the room.

While the tab indicators 126 have been described as being displayed in particular colors based on the hemodialysis machine 101 administering certain drugs, other combinations of colors can be used. For example, if certain colors have a widely known association in the medical industry with certain drugs, the tab indicators can display a color associated with a certain drug when that drug is being delivered.

While the tab indicators 126 have been described as being displayed in certain colors based on the drugs being administered, other portions or areas of the control panel can alternatively or additionally change in appearance to convey information about the drugs being administered. For example, areas of the control panel, such as areas associated with providing general dialysis system status can display descriptions (e.g., via text or color coding) related to drugs being administered.

While the tab indicators 126 have been described as being displayed in one region of the control panel that is divided into multiple portions to display information relating to multiple drugs being delivered to the patient during treatment, other configurations are possible. For example, in some implementations, the control panel has multiple regions for displaying information relating to the drugs being delivered. Each of the multiple regions can display information relating to a different drug being delivered to the patient.

While the hemodialysis system 100 has been described as determining what drug(s), if any, is/are being delivered to the patient by sending signals from the drug delivery device control unit 107 and the heparin delivery device control unit 109 to the dialysis machine control unit 103 in order to change the display of the Med Admin tab indicator 126, other techniques are possible. For example, in some implementations, the dialysis machine control unit 103 provides command signals to the drug delivery device 106 and the heparin delivery device 108 to deliver a drug and changes the Med Admin tab indicator 126 appearance based on its own command signals. The dialysis machine control unit 103 can change the Med Admin tab indicator 126 appearance automatically upon sending the command signals.

While some of the drug delivery devices have been described above as including their own control unit, the drug delivery device can alternatively or additionally be configured to communicate with a control unit of the hemodialysis machine. In certain implementations, for example, the various components of the dialysis machine, including the drug delivery device components and heparin delivery device components, are controlled by a single control unit of the hemodialysis machine.

Instead of a drug administration fluid set 110 that connects to multiple vial holders 134, 136 that hold the vials 130, 132 in place, other techniques of securing the drug delivery lines to the vials are possible. For example, in some implementation, the drug administration fluid line set can have multiple drug delivery lines that each includes a vial adapter. In such implementations, drug vial holders of the drug delivery device include recesses sized to receive the vial adapters. To spike the vials using such vial adapters, the user manually inserts each vial into the appropriate vial holders.

Figure 15:
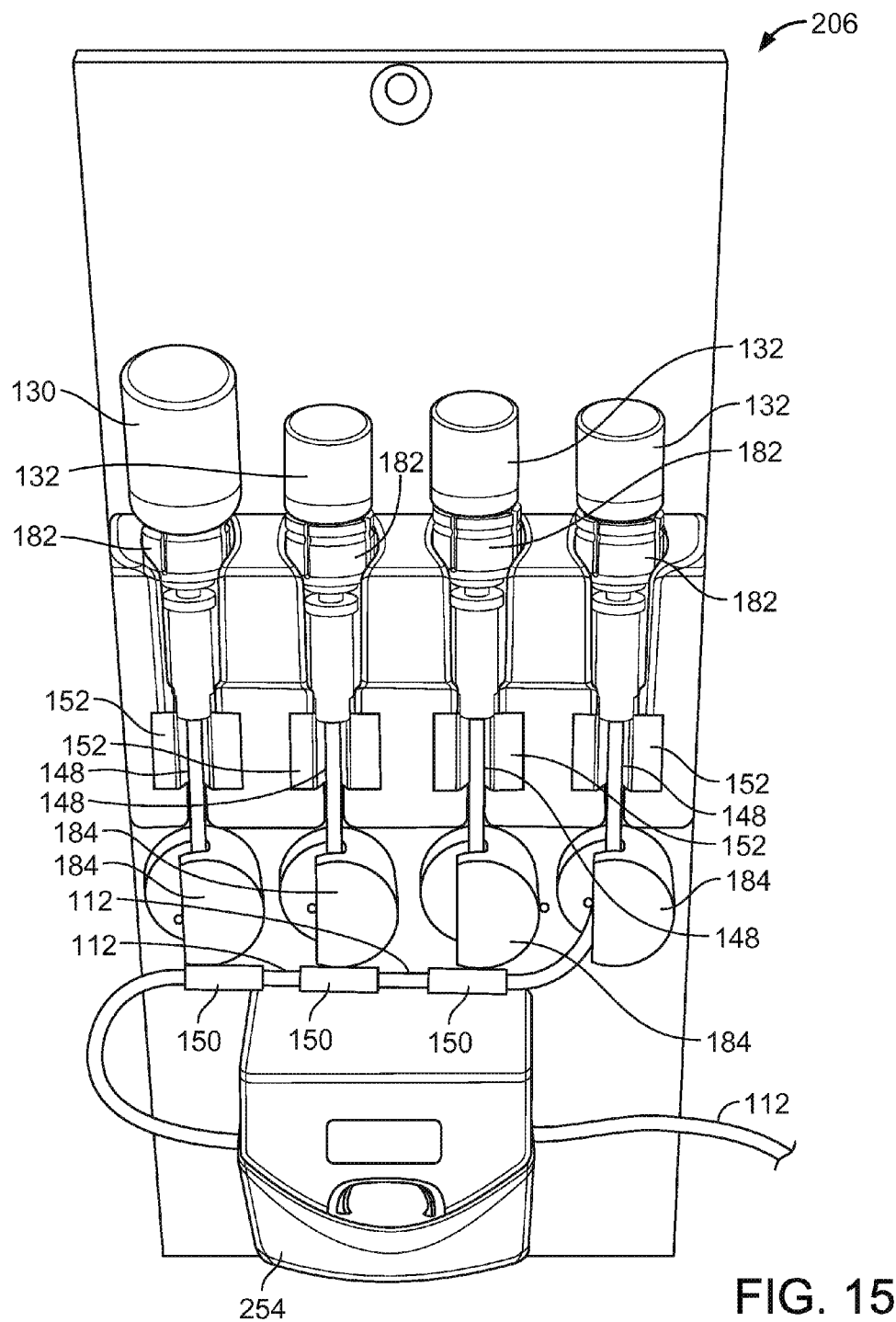
FIG. 15 is a perspective view of an alternative modular drug delivery device and a drug administration fluid line set and drug vials secured to the modular drug delivery device.

While the drug delivery device 106 has been described as having multiple pumps 154 that are each associated with a certain drug vial, other configurations are possible. For example, referring to FIG. 15, in some implementations, a drug delivery device 206 includes only one pump 254 and uses multiple occluders 184 that open and close to selectively prevent and allow drugs from the vials 130, 132 through the feeder lines 148. The feeder lines 148 are connected to the drug delivery line 112 (e.g., via t-connectors 150) so that drugs can flow to the drip chamber 116 in the drug delivery line 112.

Figure 16:
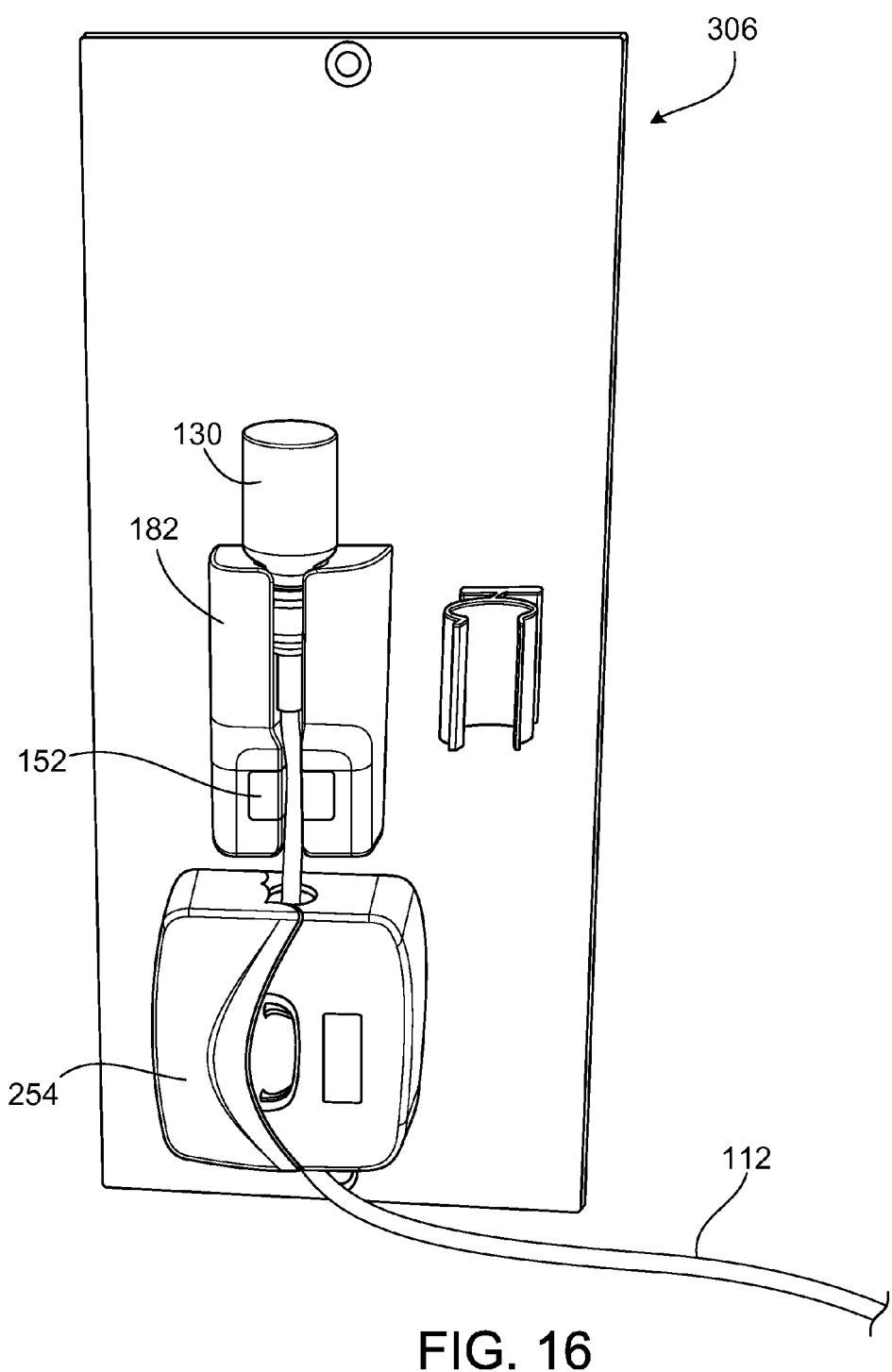
FIG. 16 is a perspective view of another modular drug delivery device that is configured for use with a single drug vial.

While the hemodialysis machine 101 has been described as including a modular drug delivery device having pumps or occluders to accommodate four drug vials, other configurations can be used. For example, the modular drug delivery device can include pumps or occluders to accommodate more or fewer (e.g., three, two, or one) drug vials. Referring to FIG. 16, a modular drug delivery device 306 includes only one pump (e.g., a Venofer pump) and a holder for securing a vial (e.g., a Venofer vial) during treatment. In some implementations, the fluid line set includes two or more drug delivery lines (e.g., one for Venofer® and one for Epogen®), each having a vial adapter, so that multiple drugs can be serially delivered to the drip chamber using the same vial holder without mixing drugs.

While the hemodialysis machine 101 has been described as including only one modular drug delivery device for delivering Venofer® and Epogen®, the hemodialysis machine can include multiple pump modules that each have only one pump. For example, in some implementations, the dialysis machine 101 includes a Venofer pump module, an Epogen pump module and a Heparin pump module that can be independently controlled using control panels on each pump module, or alternatively, by using a common control panel on the dialysis machine.

While the hemodialysis machine 100 has been described as having a control panel 104 to control and monitor the dialysis machine including drug delivery, modular drug delivery devices can include individual control panels, buttons, and display screens to control and monitor administering drugs from the drug delivery devices. Such control panels and displays would indicate drug delivery in much the same way as the control panel of the dialysis machine.

Figure 17:
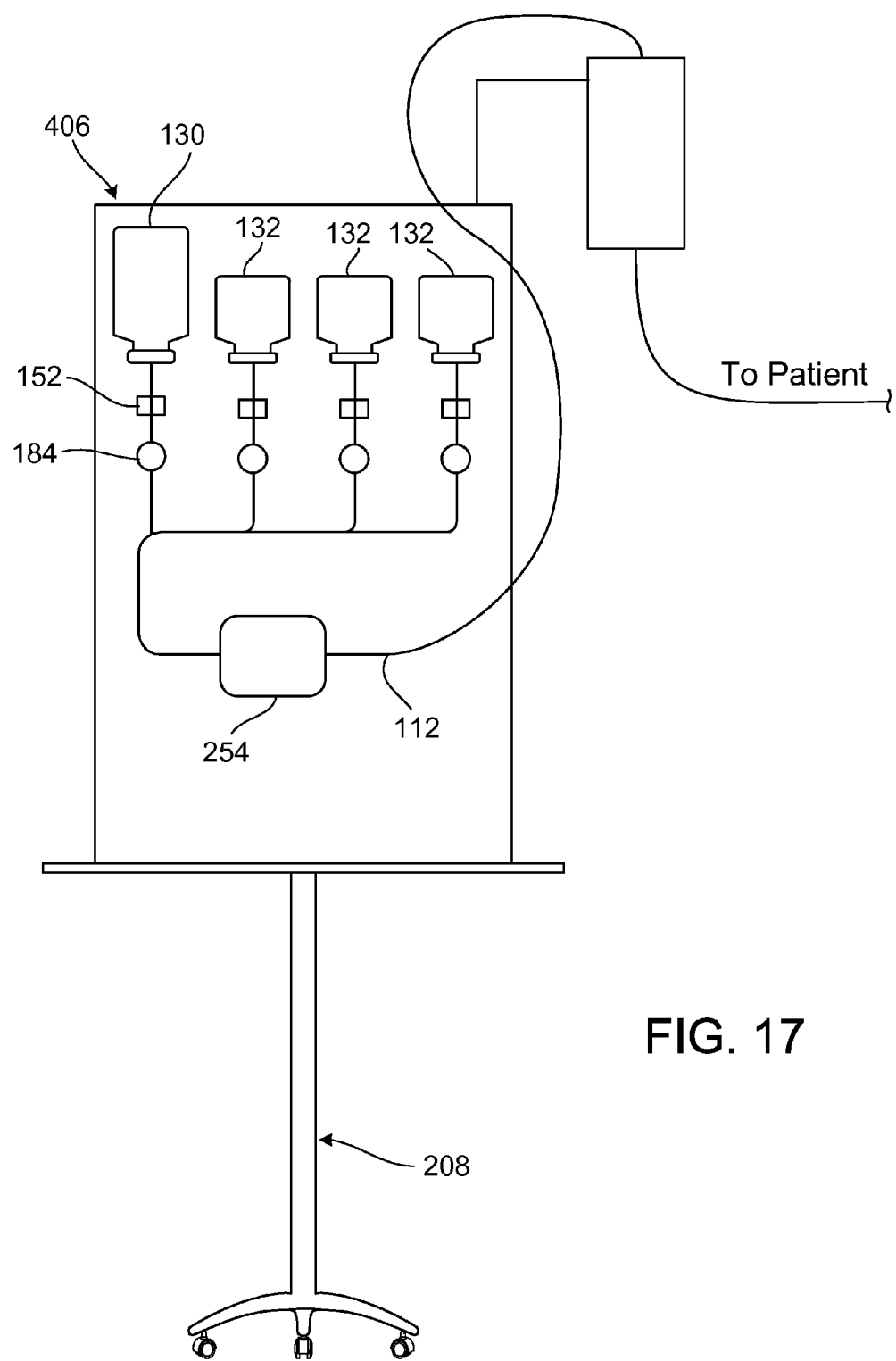
FIG. 17 is a schematic view of a standalone drug delivery system.

While certain drug delivery devices described herein are provided as components of hemodialysis machines, the drug delivery devices and methods can be used in any type of medical devices that administer drugs. Alternatively, the drug delivery devices described herein can be configured to be operated as standalone machines remotely connected to body fluid treatment systems. For example, referring to FIG. 17, a standalone drug delivery device 406 is functionally similar to the drug delivery device 206 described above with respect to FIG. 15 but sits on a wheeled cart 208 and is remotely connected to a control unit. The drug delivery line 112 of this standalone drug delivery device 406 is connected to a drip chamber 116. During use, the drug(s) is/are delivered from the vials 130, 132 to the drip chamber 116. The drug(s) is/are then delivered from the drip chamber 116 to the patient via a fluid line 114. The drip chamber 116 helps to ensure that any air pulled into the system from the vials does not reach the patient. The drug delivery device 406 can be used in a manner similar to the drug delivery device 206 described above to deliver drugs to a patient.

While certain machine setup and treatment sequences have been described, other sequences are possible. For example, in some implementations, the heparin delivery device 108 and the drug delivery device 106 are set up and the prescribed doses of heparin, Epogen®, and Venofer® are programmed prior to beginning hemodialysis treatment.

While the delivery of drugs has been described as delivering heparin slowly during the entire treatment, and Epogen® and Venofer® towards the end of treatment, other sequences are possible. For example, heparin can be administered as a bolus dose at any of various times during treatment, and/or Venofer® can be delivered prior to Epogen®.

While some of the drug delivery devices have been described as priming and delivering Epogen® and then priming and delivering Venofer®, other priming and drug delivery sequences are possible. For example, in some implementations, the drug delivery device primes all of the delivery lines associated with both Epogen® and Venofer® prior to delivering either of the drugs. By priming all of the drug lines prior to drug delivery, Epogen® and Venofer® can be delivered without requiring an additional priming step between delivering each of the drugs.

While the prescribed dosage of Venofer® and Epogen® have been described as being entered by a user, other techniques are possible. For example, in some implementations, the prescribed dosage of Venofer® and Epogen® can be electronically transmitted to the drug delivery device control unit 107 or the dialysis machine control unit 103 from a database or website accessible by the patient's prescribing physician.

While the heparin delivery device has been described as operating a syringe to administer heparin, other devices and techniques can be used.

While the control panel has been described as having certain menus to present and receive information related to hemodialysis treatment, the control panel can include different menus. For example, in some implementations, the control panel includes more or fewer menus.

While the systems and methods of identifying the administering drugs described herein have been described as being used with hemodialysis systems, the systems and methods can be used during other types of body fluid treatment processes. For example, in some implementations, drugs being administered can be identified during peritoneal dialysis treatments, blood perfusion treatments, intravenous infusion treatments, and other medical fluid handling treatments.

While the drug used during dialysis treatment have been described (e.g., heparin, Venofer, and Epogen), the systems and methods described can be used when delivering other drugs (e.g., Aranesp). Also, the specific names of drugs described as being displayed when certain drugs are being delivered can be changed or updated to reflect name changes or new drugs delivered during treatments.

While the systems and methods have been described as being used to deliver drugs commonly associated with dialysis treatments, other types of drugs can be administered and monitored. For example, Vitamin K, Vitamin D and various other types of drugs can be administered and monitored.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs (i.e., one or more modules of computer program instructions) encoded on computer storage medium for execution by, or to control the operation of, the control units or data processing apparatuses. Alternatively or additionally, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes described in this specification can be performed by one or more programmable processors executing one or more computer programs to perform actions by operating on input data and generating output. The processes can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

A number of implementations of the invention have been described. Nevertheless, it will be understood that various modifications may be made without departing from the spirit and scope of the invention. Accordingly, other embodiments are within the scope of the following claims.

What is claimed is:

1. A method comprising:
    displaying a plurality of different screens on a user interface during a treatment, at least one of the plurality of different screens being a drug delivery screen;
    displaying a plurality of different tabs on the user interface, each of the tabs being displayed regardless of which of the plurality of screens is being displayed, wherein one of the tabs is a drug delivery tab that comprises a drug identification region, the drug delivery tab being selectable to access the drug delivery screen;
    administering a first drug during the treatment, the drug identification region of the user interface having a first appearance while the first drug is being administered regardless of which of the plurality of different screens is being displayed; and
    administering a second drug during the treatment, the drug identification region of the user interface having a second appearance that is different than the first appearance when the second drug is being administered,
    wherein a first portion of the drug identification region has the first appearance and a second portion of the drug identification region has the second appearance, and the first appearance includes a first color and a first text such that a user can identify the first drug and the second appearance includes a second color and a second text such that a user can identify the second drug.

2. The method of claim 1, wherein the first and second drugs are administered simultaneously.

3. The method of claim 2, wherein, while the first and second drugs are being administered, the first portion of the drug identification region displays the first color and the second portion of the drug identification region displays the second color.

4. The method of claim 3, wherein the administration of the first drug is completed prior to completion of the administration of the second drug, and upon completion of the administration of the first drug, the drug identification region displays the second color and not the first color.

5. The method of claim 3, wherein the administration of the first drug is completed prior to completion of the administration of the second drug, and upon completion of the administration of the first drug, the drug identification region displays the second text and not the first text.

6. The method of claim 1, further comprising administering a third drug during the treatment, wherein the drug identification region has a third appearance that is different than the first and second appearances when the third drug is being administered such that a user can identify the third drug based on the third appearance of the drug identification region.

7. The method of claim 1, wherein prior to beginning administration of the first drug, the drug identification region indicates a plurality of different drugs to be delivered, and the appearance of the identification region indicates to the user that administration of the plurality of different drugs has not yet begun.

8. The method of claim 1, wherein each of the different screens is associated with one of the plurality of different tabs displayed on the user interface.

9. The method of claim 8, further comprising selecting a first one of the tabs to display a first one of the screens and selecting a second one of the tabs to display a second one of the screens.

10. The method of claim 8, wherein the tabs are located along an edge region of the user interface.

11. The method of claim 8, wherein one of the plurality of different tabs is the drug identification region.

12. The method of claim 1, wherein administering the first drug comprises delivering the first drug from a container to a drip chamber of a blood line set.

13. The method of claim 1, wherein the plurality of different screens comprises set up screens and treatment screens.

14. The method of claim 1, wherein the treatment comprises a blood processing treatment.

15. The method of claim 14, wherein the blood processing treatment is hemodialysis.

16. A method comprising:
delivering a first drug;
displaying a first screen on a user interface;
displaying a plurality of different tabs on the user interface, wherein one of the tabs is a drug delivery tab that comprises a drug identification region, the drug delivery tab being selectable to access the drug delivery screen;
while delivering the first drug and displaying the first screen, the drug identification region of the user interface has a first appearance;
while continuing to deliver the first drug, displaying a second screen on the first region of the user interface;
while continuing to deliver the first drug and displaying the second screen, the drug identification region of the user interface has the first appearance, and
delivering a second drug during the treatment, the drug identification region of the user interface having a second appearance that is different than the first appearance when the second drug is being administered,
wherein each of the tabs is displayed on the user interface regardless of which screen is being displayed, and
wherein a first portion of the drug identification region has the first appearance and a second portion of the drug identification region has the second appearance, and the first appearance includes a first color and a first text such that a user can identify the first drug and the second appearance includes a second color and a second text such that a user can identify the second drug.

17. The method of claim 16, wherein the drug identification region continuously has the first appearance while the first drug is being delivered.

18. A machine comprising:
a drug delivery device;
a graphic user interface; and
a control unit in communication with the drug delivery device and the graphic user interface, the control unit being configured to display on the graphic user interface a plurality of different screens, at least one of the plurality of different screens being a drug delivery screen and at least one of the plurality of different screens relating to a blood processing treatment, wherein the user interface includes a plurality of different tabs, each of the tabs being displayed regardless of which of the plurality of screens is being displayed, wherein one of the tabs is a drug delivery tab that comprises a drug identification region, the drug delivery tab being selectable to access a drug delivery screen,
the drug identification region including a drug identifier that indicates at least a first drug or a second drug is being administered by the drug delivery device, the control unit being configured so that the drug identifier has a first appearance when the first drug is being administered, and the drug identifier has a second appearance that is different than the first appearance when the second drug is being administered,
wherein a first portion of the drug identification region has the first appearance and a second portion of the drug identification region has the second appearance, and the first appearance includes a first color and a first text such that a user can identify the first drug and the second appearance includes a second color and a second text such that a user can identify the second drug.

19. The machine of claim 18, wherein the machine is a dialysis machine.

* * * * *

UNITED STATES PATENT AND TRADEMARK OFFICE
CERTIFICATE OF CORRECTION

PATENT NO. : 8,856,668 B2  
APPLICATION NO. : 13/335280  
DATED : October 7, 2014  
INVENTOR(S) : Michael Niesslein et al.

Page 1 of 1

It is certified that error appears in the above-identified patent and that said Letters Patent is hereby corrected as shown below:

On the Title Page, Item (56)

Column 2, line 3, after Other Publications, delete "Beirigner" and insert --Beiriger--.

Column 2, line 11, after Other Publications, delete "Fresenuis" and insert --Fresenius--.

Column 2, line 13, after Other Publications, delete "Fresenuis" and insert --Fresenius--.

Signed and Sealed this  
Seventh Day of April, 2015

Michelle K. Lee  
*Director of the United States Patent and Trademark Office*